US010373713B1

(12) United States Patent
Kello et al.

(10) Patent No.: US 10,373,713 B1
(45) Date of Patent: Aug. 6, 2019

(54) SYSTEM AND METHOD FOR PHARMACEUTICAL TRANSACTIONS

(75) Inventors: John Kello, Bloomfield Hills, MI (US); Gablan Zawaideh, Birmingham, MI (US)

(73) Assignee: BRECKENRIDGE CAPITAL LLC, Troy, MI (US)

( * ) Notice: Subject to any disclaimer, the term of this patent is extended or adjusted under 35 U.S.C. 154(b) by 334 days.

(21) Appl. No.: 12/693,573

(22) Filed: Jan. 26, 2010

(51) Int. Cl.
*G16H 40/00* (2018.01)
(52) U.S. Cl.
CPC .................................. *G16H 40/00* (2018.01)
(58) Field of Classification Search
CPC ..................................................... G16H 40/00
USPC ......................................................... 705/2–3
See application file for complete search history.

(56) References Cited

U.S. PATENT DOCUMENTS

| 6,064,968 | A * | 5/2000 | Schanz | 705/311 |
| 7,734,478 | B2 * | 6/2010 | Goodall et al. | 705/2 |
| 7,775,056 | B2 * | 8/2010 | Lowenstein | 62/127 |
| 2004/0230503 | A1 * | 11/2004 | Lucas | G06Q 10/06 705/28 |
| 2005/0177392 | A1 * | 8/2005 | Domashnev | 705/2 |
| 2008/0269947 | A1 * | 10/2008 | Beane | G06Q 20/12 700/237 |
| 2009/0083064 | A1 * | 3/2009 | Mahinda | 705/2 |

FOREIGN PATENT DOCUMENTS

JP          2007026035 A  *  2/2007

OTHER PUBLICATIONS

Translation of JP 2007026035 A.*

* cited by examiner

*Primary Examiner* — Sheetal R Paulson
(74) *Attorney, Agent, or Firm* — The Dobrusin Law Firm, P.C.; Daniela M. Thompson-Walters

(57) ABSTRACT

A system and method is disclosed for facilitating transactions involving pharmaceutical products. The system can be particularly useful for independent pharmacies, allowing them to resell pharmaceuticals that would otherwise likely expire before being used. The system can be highly automated and highly customized.

19 Claims, 26 Drawing Sheets

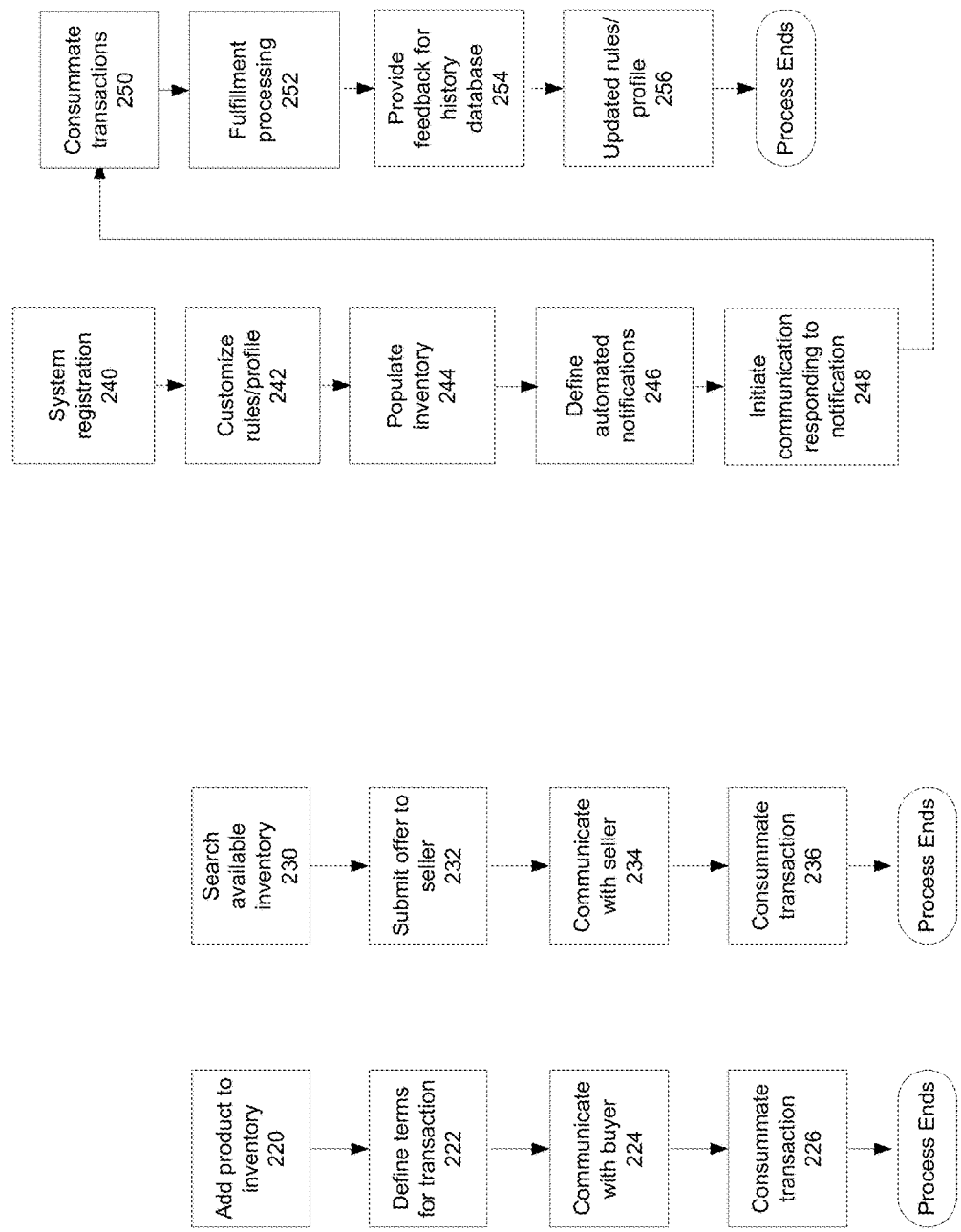

Figure 9a

| Shipping Total | Credit Total | Ship Date | Ship Method |
|---|---|---|---|
| ($32.91) | $681.93 | | FedEx Priority Overnight |
| ($32.91) | $-5.31 | | FedEx Priority Overnight |
| ($0.00) | $18.40 | | FedEx Ground |

| Ship Method | Ship Date | Expected Delivery Date | Tracking # |
|---|---|---|---|
| FedEx Priority Overnight | 01/14/2010 | 01/15/2010 | 794800105591 |
| FedEx Ground | 01/11/2010 | 01/15/2010 | 800027110031917 |

FROZEN/REFRIGERATED ITEMS MUST BE SHIPPED MON-THU VIA FedEx PRIORITY OVERNIGHT

If you are shipping a frozen or refrigerated items, remember to:

- Refrigerate/freeze products prior to packaging per manufacturer's guidelines.
- Precool an expanded polystyrene (EPS) container.
- Double bag items if shipment contains liquid or perishables that might melt or thaw.
- Arrange items compactly, but leave space around the items for coolant/dry ice.
- Seal properly.
- For additional information on shipping, please visit the Shipping Center on MatchRx.com

- For FedEx Ground shipping, DO NOT use FedEx envelopes or packages. All FedEx Ground shipments must be dropped off at an authorized drop off center. All FedEx Ground shipments picked up directly from the pharmacy is subject to a $13.00 FedEx pick up charge.

SHIPPING AGREEMENT. Shipping items must comply with the Prescription Drug Marketing Act, other laws and Sellers policies. The pharmacist whose signature appears on the signature block represents and warrants he/she is a representative or the member shown and duly authorized to certify that: (a) all saleable goods shown (1) have been stored and handled under manufacturers temperature and storage requirements while in members possession, (2) Other than information provided, has not been otherwise damaged and, (3) to the best of his/her knowledge, are saleable in accordance with applicable laws and regulations, (b) all saleable and unsaleable pharmaceutical items shown (1) were purchased from an authorized wholesaler (unless otherwise stated in writing) and (2) were not dispensed or otherwise sold by member or transferred to member from another location; and (c) contents of container agree with this form. Final credit amount may be adjusted to reflect goods that are damaged or missing or do not comply with MatchRX shipping policy. See Shipping Center a at MatchRX for instruction.

DISCLAIMER: You agree to indemnify and hold MatchRX harmless from any claim asserted by a third party that involves, relates to, or concerns any of your actions or omissions on this Order, including but not limited to your breach of the User Agreement, or your violation of any law or the rights of a third party. When shipping your prescription drug(s), it is your responsibility to comply with all applicable local, state, and federal laws, as well as statutes and regulations and the payment of any taxes.

MatchRx prohibits the direct contact of Buyers and Sellers and requires all communication to occur through MatchRx to keep consistency throughout the ordering process.

SIGNATURE: _____ DATE: _____

PRINT: _____

Match·Rx

3258 West Big Beaver Road
Suite 208
Troy, MI 48084
(877) 590-0808 toll free

BUYER'S INVOICE

SELLER: Gabe Zawaideh
Clawson Pharmacy
8383 Wilshire Boulevard
Beverly Hills, California 90211

BUYER: John Kello
Landmark Commercial Real Estate Services
27885 Halsted Road Suite 150
Farmington Hills, Michigan 48331

Order Date: 01/07/2010   Order #: 100146

INVOICE

BILLING INFORMATION

| ITEM | NAME | NDC | STRENGTH | FORM | EXP | PACK COND | PACK SIZE | PACK PRICE | QTY | TOTAL |
|---|---|---|---|---|---|---|---|---|---|---|
| 91697243 | SYETTA | 66780-0210-03 | 15 MCG/0.04ML | SOLN | 03/2012 | OR | 2.40 ML | 150.00 | 2 | 300.00 |

Product: $300.00
Shipping: $32.91
Processing: $0.00

Total Debit Amount: $332.91

BANK ACCOUNT
Account Debited: XXXXXX3456

Thank you for using MatchRx!
Questions regarding your order, please contact customer service at customerservice@matchrx.com or call 877-590-0808

SYSTEM AND METHOD FOR PHARMACEUTICAL TRANSACTIONS

BACKGROUND OF THE INVENTION

The invention relates generally to transaction systems for goods and services. More specifically, the invention is a system and method for the selling, reselling, and distributing pharmaceutical products (collectively the "system").

The healthcare industry makes up a large percentage of the U.S. economy, and it has consistently grown at a faster rate than the economy as a whole. Within the large variety of treatment options that currently exist to treat a wide variety of medical conditions, the use of pharmaceutical products plays an ever increasing role within the universe of available medical treatments. Many medical conditions that can currently be treated effectively through the use of medication would in the past have required far more invasive treatments such as surgery or chemotherapy. Compared to alternative treatment options, pharmaceutical products are often the best option in terms of effectiveness, cost-efficiency, and patient comfort.

The importance of pharmaceutical treatment options in the modern treatment of medical conditions is difficult to overstate. The pharmaceutical industry is a highly dynamic sector within the larger healthcare economy. Billions of dollars are spent each year on the discovery and testing of new medications. New uses for existing drugs are discovered and marketed each year. The regulatory approval process for pharmaceutical products is both extensive and expensive. Whether a particular disease or medical condition impacts millions of people or only a few hundred, pharmaceutical products are often the first and best line of defense for patients.

The special nature of pharmaceutical products raises a variety of unique challenges to the efficient sale, resale, and distribution of such products. Prescription medications are regulated substances that can only be sold or distributed through properly licensed entities such as pharmacies. Thus the numerous online transaction sites that are highly efficient at selling and reselling a variety of products and services simply cannot be used for the sale and resale of prescription medications. Further complicating matters is that fact that different states have different licensing requirements and different laws pertaining to the resale of prescription medications that occur between licensed pharmacies. Many aspects of the pharmaceutical industry are highly regulated and thus generic resale and other distribution approaches used by the prior art for other types of transactions are not suitable for use with pharmaceutical products. Any effective online system that facilitates the distribution or resale of pharmaceutical products will need to be cognizant of the regulatory requirements that arise when dealing pharmaceutical products. The addressing of regulatory requirements is particularly important to the degree that the system attempts to incorporate automated processing into such a system.

The purpose and nature of pharmaceutical products themselves also complicate efforts to sell, resale, or otherwise distribute them. Most products are not associated with definitive expiration dates. Books, computers, MP3 players, furniture, cars, appliances, and other common products do not significantly decay at a specific predefined point in time. In contrast, a pharmaceutical product is often comprised of a specific combination of molecules designed to have a specific impact on a particular ailment. The fragile balance embodied in many pharmaceutical products is often highly vulnerable to the passage of time. Pharmaceutical products are often associated with definitive expiration dates after which they cannot be sold and should not be used. Use of an expired pharmaceutical product can loses potency, raising significant issues pertaining to the health and safety of the patient.

Certain other products, such as food and tickets, can be associated with expiration dates. However, the aging of a pharmaceutical product is significantly different from those products. A food or beverage product may become less desirable to consumers as it approaches or even passes its listed expiration date, however the product will in most cases still function as it was intended to. In many instances, a food or beverage product may be safely and effectively used even after it has technically "expired." For example, the function of a ham sandwich is to be filling and to provide certain nutrients. Those functions are typically satisfied even if the component products are consumed after their expiration dates. A food or beverage product can be said to decay over time, but the impact of that decay to the consumer is often one of desirability, not effectiveness.

The decay of a ticket is also different from that of a pharmaceutical product, but in a manner that is opposite that of a food product. The effectiveness of a ticket for an entertainment event or a trip on an airline is not negatively impacted by the passage of time until after the event has begun or the plane has taken off, at which point the economic value of the ticket quickly drops to zero. In contrast, the decline in effectiveness and value of a pharmaceutical product occurs over a longer period of time and often in an incremental fashion.

.A variety of other attributes further distinguishes a transaction involving pharmaceuticals from transactions involving other types of products. For example, although pharmaceutical products are typically sold in a variety of package sizes to pharmacies, the pharmacies themselves often sell the product to consumers in partial units of those package sizes. In most non-pharmaceutical retail environments, the retailer does not modify or break down the package sizes of the products being sold. The pricing of certain pharmaceutical products can be subject to variety of constraints pertaining to various predefined discount levels that are influenced by third-party payor policies and payments, including but not limited insurance companies, government regulations and government payment mechanisms such as Medicare. Many pharmaceutical products require refrigeration shipping containers if they are to be transported.

The obstacles facing the efficient sale, resale, and distribution (collectively "distribution") of pharmaceutical products become particularly pronounced with relatively uncommon medicines. The prior art approaches used for the distribution of highly used pharmaceutical products are relatively efficient. For example, prescription medications for the treatment of high cholesterol are used by millions of Americans. With such high and universal demand for those products, virtually every pharmacy in the country can keep a sufficiently large supply of the product to serve its customers while being confident that the vast majority of the product will be used up prior to expiration.

Prior art distribution approaches are far less efficient with less common pharmaceutical products that are used to treat far fewer patients. Outside the context of a pharmaceutical product, the sensible business approach is to sustain an inventory of high demand items and to forego including relatively rare items in the inventory of a store. However, in the context of a pharmacy, such an inventory policy is not acceptable given the dramatic impact of going without the pharmaceutical product. Thus, unlike other businesses, a pharmacy has reasons to sustain an inventory that includes rarely purchased products. When this factor is coupled with the reality that an individual prescription typically uses only a small portion of the package size that a pharmacy purchases from a wholesaler, the prior art distribution approach for such pharmaceutical products will often result in the expiration of the product before its use. Ironically, it is the hard to find medication that often ends up as expired waste. The more esoteric the medication, the greater the challenges in avoiding the undesirable tradeoffs between wasting unused pharmaceutical products on the one hand and avoiding shortages or unavailability of the product on the other hand.

It would be desirable to avoid the waste of pharmaceutical products and facilitate access to those products by facilitating pharmaceutical product transactions in an efficient and easy to use manner.

SUMMARY OF THE INVENTION

The invention relates generally to transaction systems for goods and services. More specifically, the invention is a system and method for the selling, reselling, and distributing pharmaceutical products (collectively the "system").

The system can facilitate the ability of a pharmacy to purchase a pharmaceutical product from another pharmacy. The system can facilitate such transactions even if the buyer and seller have no pre-existing relationship or even knowledge of each other. The system can be implemented in a potentially wide variety of different embodiments and configurations.

BRIEF DESCRIPTION OF THE DRAWING

The following drawings illustrate different examples of various embodiments of the system:

FIG. 5 is a flow chart diagram illustrating an example of a seller using the system to sell a pharmaceutical product.

FIG. 6 is a flow chart diagram illustrating an example of a buyer using the system to buy a pharmaceutical product.

FIG. 7 is a flow chart diagram illustrating an example of a pharmacy registering and interacting with the system.

FIGS. 9a and 9b are in the aggregate, a screen print diagram illustrating an example of a "dashboard" that can be incorporated into the system.

FIGS. 10a and 10b are in the aggregate, a screen print diagram illustrating an example of a screen that can be used to confirm the availability of a particular pharmaceutical product in the inventory of the system.

FIGS. 11a and 11b are in the aggregate, a screen print diagram illustrating an example of a screen that can be used by a buyer to search for desired pharmaceutical products.

FIGS. 12a and 12b are in the aggregate, a screen print diagram illustrating an example of a screen that can be used by a seller to add to their inventory on the system.

Figures 13B, 13C:
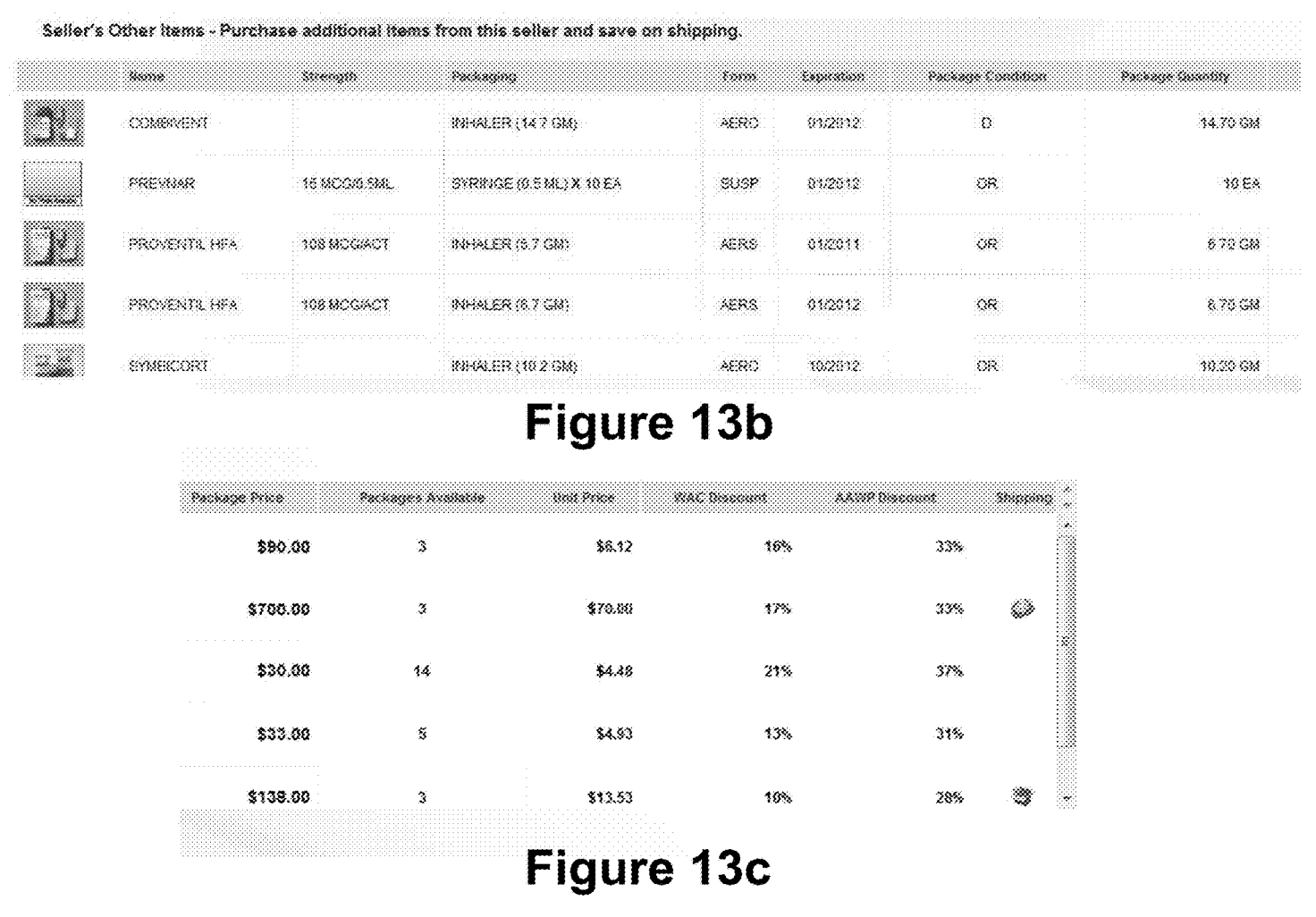

FIGS. 13a, 13b, 13c, 13d, and 13e are in the aggregate, a screen print diagram illustrating an example of screen that can be used by a buyer to display the details of a particular pharmaceutical product and additional items available from that same seller.

FIGS. 14a and 14b are in the aggregate, a screen print diagram illustrating an example of a "watchlist" screen.

FIGS. 16a, 16b, and 16c are in the aggregate, an example of a packing checklist/insert that can be generated using the system.

FIG. 17 is a screen print diagram illustrating an example of a multi-product order being displayed using the system.

FIG. 18 is a screen print diagram illustrating an example of an invoice that can be created using the system.

FIG. 19b is a screen print diagram illustrating an example of a communications screen with one of the communications being displayed in a detail view.

DETAILED DESCRIPTION

Figure 1:
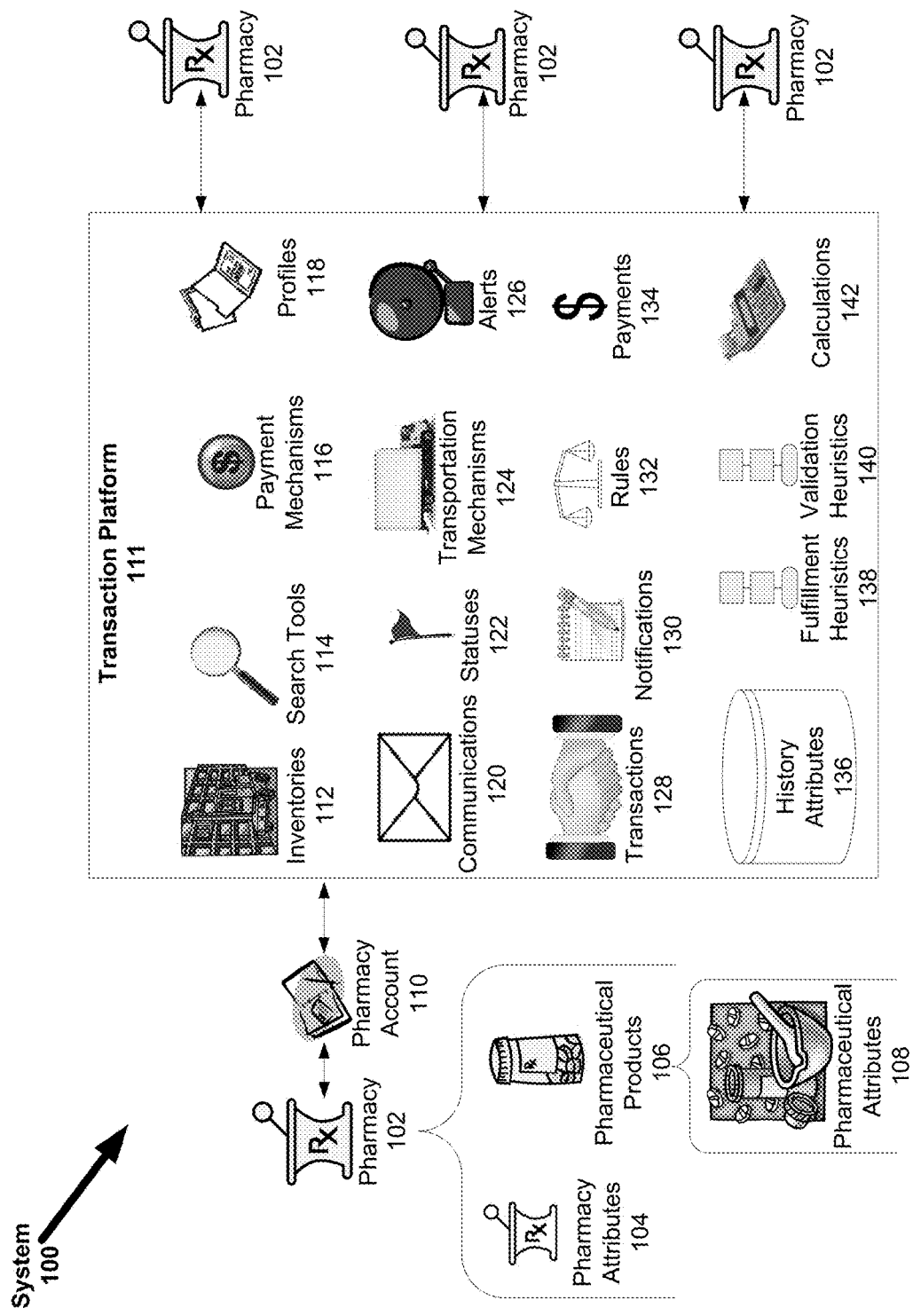
FIG. 1 is a block diagram illustrating an example of different data elements that can be processed or utilized by the system to facilitate transactions between pharmacies.

The invention relates generally to transaction systems for goods and services. More specifically, the invention is a system and method for the selling, reselling, and distributing pharmaceutical products (collectively the "system").

I. Overview

In a traditional retail environment, a merchant will typically prefer high volume items to low volume items unless the profitability of the low volume item can make up for the relatively lower volume. Such an approach is particularly desirable when the items are capable of expiration, because a relatively low volume item can be more likely to expire before it is sold, resulting in a wasted product and a financial forfeiture. Thus, in most businesses contexts, a retail merchant will focus on relatively high demand items and avoid keeping relatively low demand items in stock.

Pharmacies are often forced to either make a risky business decision by buying a quantity of a relatively low volume product or risk permanently losing a customer by forcing the customer to go elsewhere for a needed product. For reasons of reputation, a pharmacy cannot as a practically matter simply decide to carry only high volume medications in its inventory. There are many relatively low demand medications that are critical for the health and well being of patients.

Unfortunately, the need to fill pharmaceutical prescriptions to customers with uncommon ailments provides additional obstacles for the pharmacy. The pharmacy is typically required to purchase from the wholesaler a larger quantity of the product from than what is actually required from the individual customer. Given the relatively low demand for the product, it is likely that the excess quantities of the product will expire before being used, resulting in both physical waste of the product and a financial forfeiture by the pharmacy. The prior art attempts to mitigate the financial impact of the forfeiture by buying back expired pharmaceutical products for pennies on the dollar.

In contrast to the prior art, the system addresses the root cause of the problem. The system can provide a way for otherwise unconnected pharmacies to pool together some or all of their resources into a unified "virtual inventory" of pharmaceutical products. With such an approach, instead of each pharmacy purchasing a new package of a particular pharmaceutical product when it is needed, the pharmacy can look to other pharmacies and see if those other pharmacies have extra quantities available for resale. This alleviates the issue of unused products becoming expired as well as the financial impact of such waste.

The system can be implemented and configured in such a manner as to allow an individual pharmacy to determine the extent to which the particular pharmacy will participate in the functionality of the system and the nature, terms, and conditions of that participation. The individual pharmacy can decide which pharmaceutical products will be made available for sale on the system and the financial and other terms of such transactions. The system can benefit buyers and sellers alike by providing relevant historical metrics pertaining to potential transaction partner's prior usage of the system (i.e. is the party reliable, do they respond quickly to inquiries, have there been an issues in the past, etc.). By allowing users of the system to control and configure their usage of the system, overall usage of the system can be increased because the potential concerns of the pharmacy that might otherwise dissuade the pharmacy from participating can be addressed through use of the system itself.

The system can be implemented and configured in a highly automated manner. Functions such as effectuating payments through an ACH transaction or other payment mechanisms can performed in an automated manner by the system with little or no human action. Access to different shipping mechanisms can be integrated into the system, maximizing the convenience of entering into transactions and enhancing the timeliness of fulfilling consummated transactions. By utilizing data already stored on the system, errors with respect to payment and delivery information can be avoided. By integrating such functionality into the system, the system can automatically generate applicable notifications and other communications to the mutual benefit of both the buyer and the seller.

The system can be implemented and configured in such a manner that accurately factors in regulatory issues. Different jurisdictions apply different rules to sale and resale of pharmaceutical products. The system can be implemented and configured in such a manner as to facilitate compliance with those regulatory constraints. For example, by performing various validation activities "one time" at the time in which a pharmacy obtains an account with the system, the system avoids the need to perform redundant inquiries at the time of each individual transaction. Once an account is obtained with the system, validation of that account on an ongoing basis can be performed in the background on an automated basis. With respect to states in which a wholesale license is required for the sale of a pharmaceutical product to a pharmacy, the system can allow an entity with the required licensing credential to participate in the system. For example, in the context of the system operated by an application service provider ("ASP"), the ASP could obtain the requisite license so that the system itself could serve as an authorized go-between for what is otherwise a pharmacy to pharmacy transaction. The system can be used to store information and documentation pertaining to regulatory compliance. The system can also be used to track and generate a variety of history-based metrics that pertain to regulatory compliance.

Use of the system can be particularly beneficial for independent pharmacies or relatively small groups of related pharmacies, because those pharmacies typically have relatively small aggregate inventories and are less likely to have cutting edge information technology tools for the management of their respective product inventories. The system can be implemented as a web-based online transaction system that is operated and managed by an ASP. The system can be implemented in a wide variety of different alternative technical and business configurations. For example, with respect to ASP embodiments, the system could be provided free of charge, with the only charge assessed to users being a transaction-based charge paid by the seller and/or buyer. Other ASP embodiments could involve the payment of a monthly subscription fee, with users being allowed to perform an unlimited number of transactions at no charge. With respect to non-ASP embodiments, the system could be implemented and operated by wholesalers, reverse distributors, individual pharmacies, or associations comprised of individual pharmacies.

The system can configured to interface with a wide variety of other related business management technologies. In many embodiments, the system can be integrated with other internal and external information technology systems, such as payment mechanisms, inventory management tools, scheduling applications, communication systems, customer relation management applications, and a wide variety of other tools used to manage the operations of the pharmacy.

The system can be implemented to allow sellers to "push" transactions as well as to allow buyers to "pull" transactions.

II. Introduction of Elements and Definitions

The system can be implemented in a wide variety of different embodiments, configurations, and contexts. In accordance with the provisions of the patent statutes, the principles and modes of operation of this invention have been explained and illustrated in a variety of embodiments and configurations. However, it must be understood that this invention may be practiced otherwise than is specifically explained and illustrated without departing from its spirit or scope. The system can be implemented in a wide variety of different configuration using a wide variety of different information technology and other components in the processing of a wide variety of different elements and heuristics.

FIG. 1 is a block diagram illustrating an example of different data elements that can be processed or utilized by the system 100 to facilitate transactions between pharmacies 102. In the example provided in FIG. 1, the system 100 is a tool by which pharmacies 102 interact with each other through their participating in the system 100. The system 100 facilitates transactions 128 involving pharmaceutical products 106, including but not limited to prescription medications. The system 100 functions to facilitate interactions between various entities, including but not limited to pharmacies 102. For example, the system 100 can potentially be implemented to allow participation by manufacturers, researchers, wholesalers, reverse-distributors, hospitals, health plans, government agencies, physician practice groups, and other entities. For example, in some embodiments of the system 100 the functionality of the system 100 is integrated with an electronic prescription service, with the filling out of a relatively low volume prescription automatically triggered a communication 120 to the applicable pharmacy 102 to initiate procurement of the needed medication product 106. Integration of the system 100 with various IT applications providing for inventory management, payment mechanisms, transportation/shipment mechanisms, electronic prescription application, online medical records, automated certification systems, and other resources can provide valuable additional benefits to users 150 of the system 100.

A. Pharmacy

The system 100 can be used to allow pharmacies 102 to more easily interact with each other, and engage in transactions 128 involving pharmaceutical products 106. A pharmacy 102 is typically a retail merchant whose business includes selling pharmaceutical products 106, including but not limited to prescription medications. Operation of a pharmacy 102 requires a duly authorized license from the applicable jurisdiction. In some instances, a pharmacy 102 is affiliated with a hospital. In other instances, a pharmacy 102 could be affiliated with a health plan or have a relationship with a particular physician practice group. A wide variety of different entities can potentially utilize the system 100 to interact with each other. However, the original inspiration for the design of the system 100 was to allow pharmacies 102 to interact with each other even if those pharmacies 102 had no relationship with or knowledge of the potential transaction partner.

In some embodiments of the system 100, only pharmacies 102 can engage in transactions using the system 100. However, unless otherwise prohibited by a regulatory constraint, there is no reason why a company that also operates as a wholesaler, a medical plan, a physician practice group, or even a pharmaceutical manufacturer could not also operate as a licensed pharmacy 102, and thus participate in the system 100 as a pharmacy 102. Other roles or activities of a pharmacy 102 participating in the system 100 can be relevant from the standpoint of regulatory compliance. However, the key requirement for participation in many embodiments of the system 100 is the status of a licensed pharmacy. However, subject to potential regulatory constraints, some embodiments of the system 100 could allow for non-pharmacies to participate in the system 100 in a variety of different ways.

The illustration of FIG. 1 includes only four pharmacies 102 due to space limitations. However, the system 100 can be implemented with a potentially unlimited number of participating pharmacies 102. The greater the number of participating pharmacies 102, the greater the size and value of the aggregated "virtual inventory" that can be accessed through the system 100.

The system 100 can be configured in a variety of different ways to encourage pharmacies 102 to participate in the system 100. For example, pharmacies 102 could be allowed to register with the system 100 at no charge. The charging of fees could be limited to transaction fees that are charged only when a desirable transaction is actually consummated. Participation in the system 100 can also be facilitated by giving each pharmacy 102 as much control over their interactions with the system 100 and the other participating pharmacies 102 as possible through the use of configurable rules and preferences. The greater the degree to which the system 100 allows individual pharmacies 102 to customize and configure how the system 100 operates with respect to that pharmacy 102 the more likely it is that the pharmacy 102 will make productive use of the system 100 to the fullest extent possible. Automated processing that makes the system 100 convenient to use can also enhance the number of participating pharmacies 102, increasing the value that the functionality of the system 100 can provide to those pharmacies 102.

A single pharmacy 102 can have more than one pharmacy account 110 and more than one user 150. The system 100 can be configured in a highly configurable manner allowing pharmacies 102 to influence how processing occurs with respect to the particular pharmacy 102. For example, different pharmacies 102 can establish different processing rules 132, configure different types of notifications 130, create different template communications 120, and define different statuses 122 that can be used as triggers to influence automated processing by the system 100.

B. Pharmacy Accounts

Due to the highly regulated nature of pharmacies 102 and the sale of pharmaceutical products 106 such as prescription medications, many embodiments of the system 100 will require the participating entities to establish verified accounts (such as a pharmacy account 110) before being allowed to view information on the system 100 or otherwise participate in transactions using the system 100. Different embodiments of the system 100 can utilize a variety of different enrollment or registration processes that involve different degrees of automation and validation. In some embodiments of the system 100, the system 100 can be configured communicate directly with government databases to confirm the licensing information of a particular pharmacy 102. In many embodiments of the system 100, critical licensing information and documentation can be stored on one or more database 160 utilized by the system 100. Even enrollment procedures that require human intervention can benefit from predefined checklist requirements that are automatically enforced through the processing of the system 100. To accommodate different regulatory rules in different jurisdictions, the validation heuristics 140 used to validate a pharmacy account 110 can similarly vary from jurisdiction to jurisdiction.

Some embodiments of the system 100 can be configured to allow a pharmacy 102 to participate in a particular transaction without having an ongoing account 110 that is registered with the system 100. However, such embodiments will typically need to perform one or more validation heuristics 140 pertaining to the particular non-registered pharmacy 102 each time that pharmacy 102 seeks to engage in a transaction. In many circumstances and for a multitude of reasons, it makes sense to either require each participating pharmacy 102 to create an ongoing account 110 or to at least encourage pharmacies 102 to do so.

A single pharmacy account 110 can involve multiple pharmacies 102 and multiple users 150. A pharmacy account 110 can be associated with specific payment mechanisms 116, transportation mechanisms, delivery addresses, and different data elements processed by the system 100.

C. Transaction Platform

Figure 2:
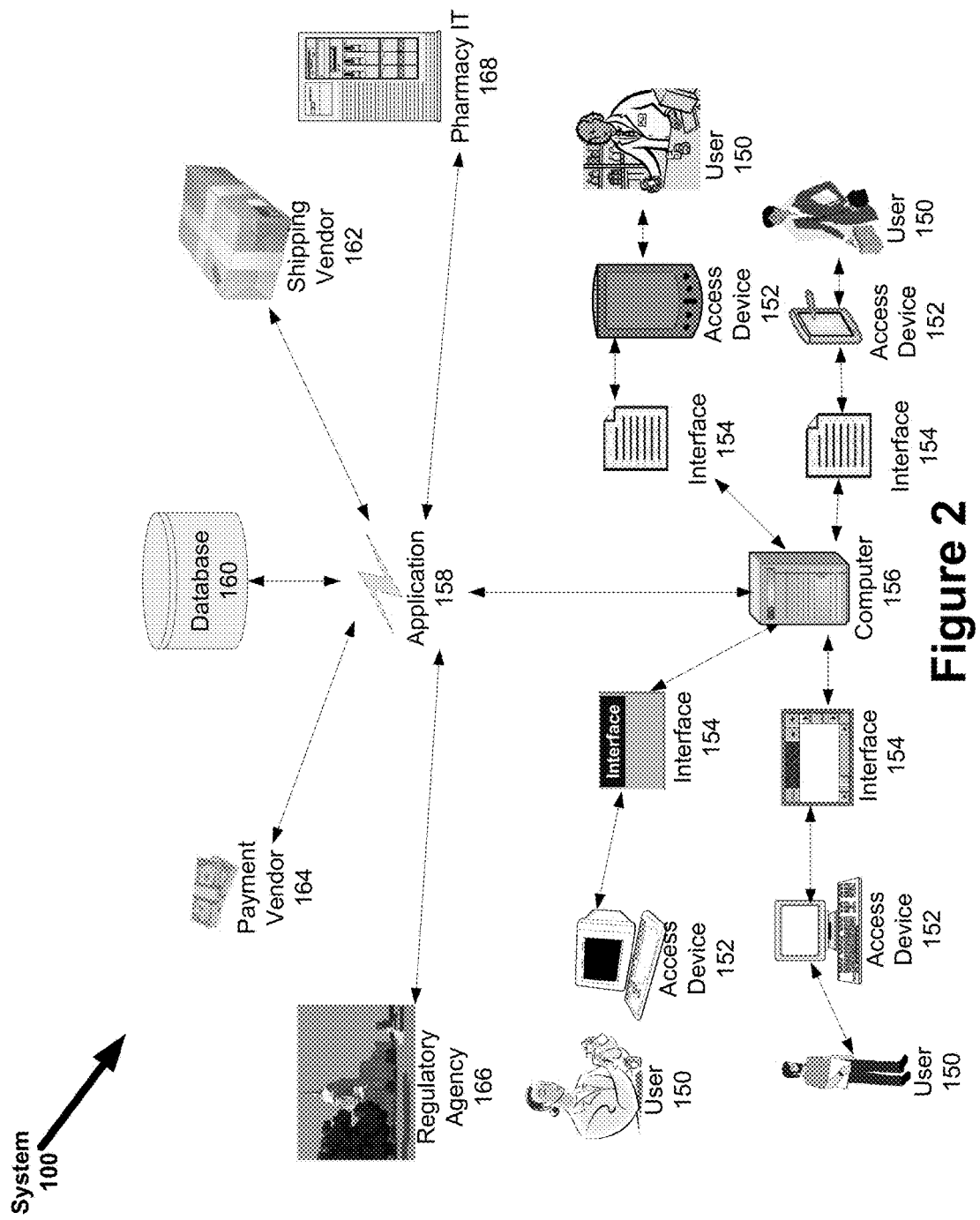
FIG. 2 is an environmental diagram illustrating an example of some information technology components that can be incorporated into the system.

As illustrated in FIG. 1, pharmacies 102 interact with each other through a transaction platform 111 used by the system 100 to facilitate such interactions. The transaction platform 111 can be configured in a wide variety of different ways with a wide variety of different components. Some examples of information technology components are illustrated in FIG. 2 and are discussed below. The transactions platforms 111 used by the system 100 can be organized and configured in a wide variety of different combinations of servers such a s computers 156, databases 160, access devices 152, interfaces 154, network connections, and interfacing IT systems.

D. Processing Elements

Much but not all of the functionality of the system 100 resides within data elements processed by the transaction platform 111. Some data elements such as a search tool 114 or a communication 120 can exist solely as "virtual" elements or components within the transaction platform 111. Other data elements such as pharmaceutical product 106 or a pharmacy 102 may exist as "virtual" data elements within the system 100, but such elements also maintain an independent physical existence outside the transaction platform 111. For example, unlike a video game or a downloaded video game or song, a pharmaceutical product cannot be transmitted electronically. Instead it must be shipped or otherwise transported in the non-virtual world. Still other elements or components of the system 100 exist solely in the physical world. For example, a printed label placed on a package or a sticker place a product container to indicate that a particular pharmaceutical product 106 has been logged into the "virtual inventory" 112 of the system 100 exist in the physical world. It can be important to understand the different ways in which different components and elements within the system 100 exist and function.

1. Categories of Data Elements

The system 100 can be configured to operate in a highly nuanced and context specific manner. Virtually any attribute that could rationally impact the decision making of a pharmacy 102 using the system 100 can be incorporated into the system 100 as a data element processed by the system 100. The system 100 can create, update, access, and delete a wide variety of data elements, including entity-based attributes, product-based attributes, transaction-based attributes, and system-based attributes. Different embodiments of the system 100 can be configured to distinguish between highly complex differences in data elements.

a. Entity-Based Attributes (Pharmacy Attributes)

Some information used by the system 100 relates not a particular pharmaceutical product 106 and not to a particular transaction 128, but rather to a particular entity. For example, the licensing information for a particular pharmacy 102 is specific to the pharmacy 102, and does not vary with the transactions 128 that the pharmacy 102 enters into. Any attribute of a pharmacy 102 that is potentially relevant to any function of the system 100 (regardless of how frequent or infrequent the information would actually influenced the processing performed by the system 100) can be stored as a pharmacy attribute 104. Pharmacy attributes 104 will typically be stored in relation to a particular pharmacy account 110, although the system 100 can be implemented in such a manner that would allow a single pharmacy 102 to have more than one pharmacy account 110.

Examples of potentially relevant pharmacy attributes 104 can include: licensing information; licensing documentation; years in business; number of employees; delivery addresses; contract information; ownership information; jurisdictional location; one or more payment mechanisms 116 such as bank accounts, credit cards, and other financial accounts; one or more profiles 118 that can be viewed by other participating pharmacies 102 (such profiles 118 may or may not be linked to specific access criteria defined by the pharmacy 102); one or more alerts 126 defined by the pharmacy 102 with respect to its activities on the system 100; one or more notifications 130 configured by the pharmacy 102 with respect to its use of the system 100; DEA license number; NPI number; state license number; state license number expiration date; historical metrics 136 pertaining to past interactions with the system 100; feedback from transaction partners; number of locations; credit rating; various financial metrics; and potentially any other characteristic of a pharmacy 102.

b. Product-Based (Pharmaceutical) Attributes

A pharmaceutical attribute 108 can be virtually any characteristic of a pharmaceutical product 106, including but not limited to prescription medications, that can be relevant to the facilitation of transactions through the system 100. The system 100 can be configured to be cognizant of virtually any pharmaceutical attribute 108 that can be potentially relevant to the functionality of the system 100.

Examples of pharmaceutical attributes 108 can include: owner; availability for sale on the system 100; name; generic name; strength; form (i.e. capsule, tablet, liquid, etc.); known side effects; general descriptions of efficacy; expiration date; packaging; package condition; package quantity; classification (i.e. FDA Schedule); price; unit price; available packages; WAC discount; AAWP discount; NDC code; package size; lot number; available packages; chemical formulas; use instructions; discount type; discount rate; classification; and other relevant data.

c. Transaction-Based Attributes

Any attribute or characteristic of a transaction 128 can potentially constitute a transaction attribute that the system 100 is configured to create, store, update, and delete as applicable. The system 100 can be configured to be cognizant of virtually any transaction attribute that can be potentially relevant to the functionality of the system 100.

Examples of transaction attributes can include: account number, profile 118, or other indicia of the identities of the buyer and seller; pharmaceutical products 106 included in a transaction 128 and their relevant pharmaceutical attributes 108; communications 120 and notifications 130 used in consummating the particular transaction 128; payment mechanisms 116 used to fulfill the particular transaction; transportation mechanisms 124 used to ship the applicable pharmaceutical products 106; payments 134 made; prices charged; changes in status 122 throughout the transaction process; calculations 142 pertaining to the transaction; and any other attribute that is specific to a transaction 128.

d. Process-Based or System-Based Attributes

Any attribute or other type of information that is processed by the system 100 or that can influence the processing of the system 100 but is not a pharmacy attribute 104, a pharmaceutical attribute 108, or a transaction attribute is a process attribute, i.e. a data point created by the system 100 in performing its processing that can itself influence subsequent processing.

Examples of process attributes can include: results generated through the use of various manual and/or automated search tools 114; a communication 120 such as an e-mail, phone call, text message, instant message, fax, or letter; a change in status 122; a change in available transportation mechanisms 124 or payment mechanisms 116; alerts 126 or notifications 130 used to trigger subsequent processing; rules 132 impacting how a single pharmacy 102 or groups of pharmacies 102 interact with the system 100; history attributes 136 relating to potentially any use of the system 100; fulfillment heuristics 138 applied by the system 100 in the fulfillment of transactions 128; validation heuristics 140 applied in the validation of the regulatory compliance of pharmacies 140; and potentially any other data point generated by system 100 that can influence the subsequent processing performed by the system 100.

2. Examples of Data Elements

The system 100 can incorporate a wide variety of different data elements into the processing of the system 100.

a. Inventories

An inventory 112 is a collection of products 106 of which the system 100 is cognizant of. Each pharmacy 102 has its own inventory 112 of products 106 that it has entered onto the system 100. The system 100 itself has an aggregate inventory 112 of all pharmaceutical products 106 entered onto the system 100. The aggregate volume of a particular pharmaceutical product 106 entered onto the system 100 constitutes the inventory 112 of that product 106 on the system 100.

Inventory 112 levels and changes to the different types of inventory 112 can be used by the system 100 to impact the processing of the system 100. For example, the price sought by a particular seller can be configured to automatically increase (either by a fixed amount or a percentage) based on a reduction of the availability of the product 106 on the system 100. Conversely, the price desired by a particular buyer could be configured to automatically decrease (by a fixed amount or a percentage) when inventory 112 of a particular product 106 is added to the system 100.

b. Search Tools

A search tool 114 is a means by which a user 150 obtains targeted information of interest to the user 150. Search tools 114 can potentially be used to obtain pharmacy information attributes 104, pharmaceutical attributes 108, transaction 128 attributes, and process attributes. Some embodiments of the system 100 may store searches as history attributes 136 for a variety of purposes. Some embodiments of the system 100 may utilize search information for automated price adjustments in a manner similar to how inventory 112 changes can also be used to influence buy/sell pricing. Virtually any type of attribute that the system 100 is cognizant of (including but not limited to pharmaceutical attributes 108) can potentially be used as search criteria for the search tool 114.

c. Payment Mechanisms

A payment mechanism 116 is a manner of providing payment. Many embodiments of the system 100 will be configured to allow the seller to determine what types of payment mechanisms 116 the seller is willing to accept, either on an on-going basis or with respect to a particular transaction 128. A buyer can similarly define payment mechanisms 116 that the seller is willing to use.

In preferred embodiments of the system 100, online payment mechanisms 116 such as the processing of a credit card charge, a wire transfer, or an ACH financial transaction can be initiated in an automated manner without any human intervention after a proposed transaction 128 is agreed to by both parties through use of the system 100.

d. Profiles

A profile 118 is comprised of pharmacy attributes 104 that a pharmacy 102 has decided to make accessible to other pharmacies 102. A single pharmacy 102 can have more than one profile 118. In some embodiments of the system 100, criteria based rules 132 are defined to automatically allow certain pharmacies 102 and users 150 to access more detailed versions of a profile 118 than other pharmacies 102 and users 150. In a preferred embodiment of the system 100, a pharmacy 102 is given significant control over the extent that information about the pharmacy 102 is allowed to be accessed by other pharmacies 102 and their users 150. Profiles 118 can be associated with individual users 150 as well as with the pharmacies 102 with whom the users 150 are associated with.

e. Communications

A communication 120 is an exchange of information between two users 150. Many communications 120 can however be automatically generated on behalf of one user 150 and then be automatically sent to another user 150. Communications 120 are typically exchanged between a buyer and a seller in different stages of a contemplated transaction 128. Communications 120 are typically either transaction attributes and/or process attributes. Examples of communications 120 include e-mail, faxed correspondences, traditional letters, instant messages, text messages, MP3 and other audio/voice mail messages, telephone calls, and video conferencing/messages.

f. Statuses

A status 122 is an attribute that relates to the condition or state of another attribute of which the system 100 is cognizant of. A status 122 can relate to a pharmacy attribute 108 (for example, a pharmacy can be associated with an expired license), a pharmaceutical attribute 108 (for example, a product 106 may not be available for sale), a transaction attribute (for example, a transaction may not yet be consummated), or a process attribute (for example, changes to a rule 132 may be pending).

Statuses 122 are used to facilitate automated processing. The more that an embodiment of the system 100 provides opportunities to sophisticated automation, the more that such an embodiment will need to provide opportunities to define various statuses 122 and rules 132.

g. Transportation Mechanisms

A transportation mechanism 124 is potentially any manner of delivering one or more pharmaceutical products 106 sold in a transaction 128 to the buyer. Many embodiments of the system 100 will be configured to allow the seller to determine what types of transportation mechanisms 124 sellers and/or buyers are willing to utilize. In many embodiments of the system 100, the available transportation mechanisms 124 will include at least one private courier with the capability of providing overnight delivery and online tracking.

h. Alerts

An alert 126 is similar to a notification, except that it is generated by a rule 132 set by the system 100 or an administrator rather than any input by a user 150 or pharmacy 102.

i. Transactions

A transaction 128 is a contractual agreement between two or more parties through use of the system 100 for the sale of one or more pharmaceutical products 106. As discussed above, a transaction 128 can include a wide variety of relevant transaction attributes.

j. Notifications

A notification 130 is similar to a communication 120 except that it occurs between the system 100 to a user 150 or pharmacy 102, and not from one user 150 or pharmacy 102 to another user 150 or pharmacy 102.

Notifications 130 are typically triggered by user-defined criteria in the form of various rules 132. When the applicable contextual triggers defined by the application rules 132 occur, the notification 130 is sent. For example, a notification 130 could be triggered when a particular pharmaceutical product 106 is added to the aggregate inventory 112 of the system 100. The system 100 can be implemented in a highly configurable manner that supports highly nuanced notification 130 triggers.

Notifications 130 can be triggered by omissions as well as actions. In many embodiments, notifications 130 are triggered by complex compound criteria requiring multiple triggering events or omissions.

k. Rules

The system 100 can be configured in such a manner as to support a wide range of different types of rules 130. Some rules 132 are applied system-wide and are set by the operator of the system 100, such as an ASP. Other rules 132 are defined by individual pharmacies 102 even individual users 150. A rule 132 defined by a pharmacy 102 or user 150 can be limited in application to a specific transaction 150 or a specific product 106 in certain cases, while being applied pharmacy-wide or user-wide in other cases. Rules 132 can be defined and enforced with respect to pharmacy attributes 104, product attributes 108, transaction attributes, and/or process attributes. The system 100 can use rules 132 to automate virtually any action that could otherwise be performed in a manual manner by a user 150 or pharmacy 102.

l. Payments

A payment 134 is a transfer of money. Payments are typically made from buyers to sellers, although alternative arrangements are possible. As discussed above, a wide variety of different payment mechanisms 116 can be utilized by the system 100. In some embodiment of the system 100 that are operated by an ASP, participating pharmacies 102 are charged a fixed service charge by the ASP when they sell one or more pharmaceutical products 106 to another pharmacy 102 using the system 100.

m. History Attributes

Virtually any information stored at any time by the system 100 can be stored as a historical attribute 136 for reference on a going forward basis. History attributes 136 can be particularly useful when the system 100 seeks to provide incentives for effective use of the system 100. For example, pharmacies 102 that make greater use of the system 100 or pharmacies 102 that quickly deliver purchased products 106 can be associated with a history-based rating that favorably distinguishes them from infrequent or more problematic pharmacies 102. The greater the ability of users 150 and pharmacies 102 to defined highly nuanced and customizable rules 132, the greater the potential impact of storing history attributes 136 and making them accessible to the system 100.

n. Fulfillment Heuristics

In order to expedite the fulfillment of transactions 128, the system 100 can support the ability of users 150 and/or pharmacies 102 to define automated fulfillment heuristics 138 that can then be performed without human intervention in the applicable transaction 128. For example, if a particular pharmacy 102 has an account with a particular transportation mechanism 124 and a particular payment mechanism 116, the fulfillment of a transaction 128 can automatically invoke those mechanisms. Mailing labels can be automatically printed for the shipping container, invoices automatically generated, payments 134 automatically made at the predefined time, confirmation communications 120 created and sent out, etc.

o. Validation Heuristics

As discussed above, pharmacies 102 are highly regulated businesses and the sale of pharmaceutical products 106 is not equivalent to selling a book or a used stereo system. The system 100 can implement a variety of either fully automated or partially automated validation heuristics 140 to validate that a particular user 150 or pharmacy 102 is in fact entitled to participate in the system 100, as well as any corresponding limitations to that participation.

p. Calculations

The system 100 can use a variety of calculations 142, particularly with respect to pricing, in the process of forming and fulfilling transactions 128. For example, price discounts can be defined as percentage discounts from objective price metrics, such as WAC or AAWP.

III. Environmental View and Components

FIG. 2 is an environmental diagram illustrating an example of some information technology components that can be incorporated into the system 100 and used to facilitate various different data elements that can be incorporated into the processing performed by the system 100. The system 100 can incorporate a wide variety of different information technology components and architecture configurations in providing the functionality of the system 100.

A. Users

A user 150 is typically a human being who interacts with the system 100 on behalf of an organization, such as a pharmacy 102 or an ASP that operates and maintains the system 100. Expert systems, automated intelligence applications, neural networks, and other types of artificial intelligence technologies can also potentially act as users 150 with respect to the system 100.

A user 150 who is given authority over other users 150 associated with the same entity is an administrator. A user 150 with administrative authority over the entire system 100 and not merely a participant is a system administrator. An individual user 150 can be associated with a profile 118 that is distinct from the profile of the pharmacy 102 with which they are associated with.

B. Access Devices

Any device 152 that allows for a user 150 to interact with the system 100 can constitute an access device 152. Some access devices 152 may provide only limited interactions, while others allows the user 150 full access to the functionality of the system 100. As illustrated in FIG. 2, a wide variety of different access devices can be incorporated into the system 100. Examples of access devices 152 include desktop computers, laptop computers, notebook computers, tablet computers, cell phones, personal digital assistants ("PDAs"), mainframe terminals, notepad computers, pagers, telephones, scanners, web cams, and fax machines.

C. Interfaces

An interface 154 is virtual boundary between the system 100 and an access device accessing the system 100. The interface 154 is influenced by both the system 100 and the access device 152. Examples of interfaces 154 include graphical user interfaces, web pages, automated phone systems, automated scanners, and software applications common referred to as operating systems.

The interfaces 154 of the system 100 can be influenced, configured, and customized in accordance with the attributes of the pharmacy 102 as well as in some instances, the attributes of the user 150. The interfaces 154 of the system 100 appear differently to different pharmacy accounts 110 and different users 150.

D. Computer

A computer 156 is an electronic device with a processor that houses and/or runs the application 156. In many instances, one or more server computers 156 will be used to host the application(s) 158 that include the electronic instructions that enable the system 100 to function.

E. Application

An application 158 is a computer program and relates files such as linked libraries that comprise the various instructions for a processor to perform the functionality of the system 100. The application 158 is typically written in some form object-oriented programming language such as Java although any type of programming language can be used.

F. Database

A database 160 is a software tool used to store information. One or more Standard Query Language ("SQL") databases are typically used to store, update, modify, and delete the data used by the system 100. A wide variety of data storage techniques can be used as databases, including object databases, hierarchical databases, and various types and combinations of flat files and data structures.

G. Shipping Vendor

The system 100 can be configured in such a manner to interface with outside entities and information technology ("IT") configurations. For example, the application 158 can interface directly with the IT architecture of a shipping vendor to facilitate an efficient, accurate, and easy to use fulfillment processes when it comes to the shipping of products 106 from sellers to buyers.

H. Payment Vendor

The system 100 can also be configured to facilitate interfacing between the application 158 of the system 100 and the IT architecture of the payment vendor 164 to facilitate an efficient, accurate, and easy to use payment process as part of the fulfillment heuristics 138 of the system 100.

I. Regulatory Agency

The application 158 can interface directly with IT resources such as databases hosted by various regulatory agencies 166. This can enhance the ability of the system 100 to confirm that a particular pharmacy 102 is duly licensed and to propagate the appropriate changes to system 100 processing that result from changes in license status 122 or even regulatory rules 132.

J. Pharmacy IT

Pharmacies 102, whether individual independent pharmacies 102 or small to large groups of related pharmacies 102 rely on various IT applications to facilitate the pursuit of their business objectives. The application 158 used by the system 100 can interface with those applications 168. For example, an inventory management tool used to manage the entire inventory of the pharmacy 102 can be integrated into the system 100 to make it easier for that pharmacy to sell products 106 using the system 100. Client relationship management tools, scheduling applications, and other technologies can also be integrated or interfaced with the application(s) 158 used to provide the functionality of the system 100.

IV. Subsystem-Views

The system 100 can be implemented in a wide variety of subsystem configurations. As discussed above, the variety of different information technology architectures that can be used to implement the system 100 are nearly limitless. While the organizational structure of what functions are provided can be varied, the functional capabilities of the system 100 can be organized into a finite number of subsystems or modules.

A. Subsystem Configuration #1

Figure 3:
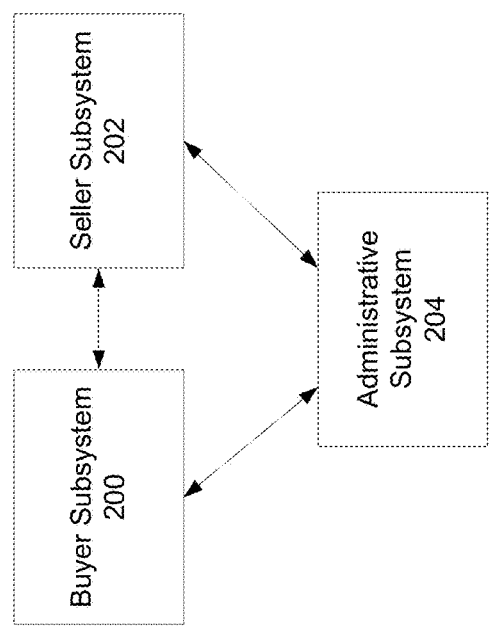
FIG. 3 is a block diagram illustrating an example of a subsystem-level view of the system.

FIG. 3 is a block diagram illustrating an example of a subsystem-level view of the system 100. As illustrated in FIG. 3, the functionality of the system 100 can be characterized as a collaboration between a buyer subsystem 200, a seller subsystem 202, and an administrative subsystem 204.

1. Buyer Subsystem

A buyer subsystem 200 can be used to perform any activity by a buyer seeking to purchase a pharmaceutical product 106 through use of the system 100. A search tool 114 can be used in conjunction with a wide range of criteria to identify potential buying opportunities, including any pharmaceutical attribute 108. The process can include process attributes as well as transaction attributes, pharmacy attributes 104, and pharmaceutical attributes 108.

The buyer subsystem 200 can be used to set up ongoing notifications 130 based on automatically performed searches. Calculations 142 can be performed pertaining to minimum discount requirements calculated from AAWP and WAC prices. The buyer subsystem 200 can also be used to generate follow-up communications 120 with sellers, and to perform the various fulfillment processes that must be performed in order to complete an agreed to transaction 128. The buyer subsystem 200 can also be used to facilitate payments 134 to sellers through the use of various payment mechanisms 116. A buyer subsystem 200 can be used to define a profile 118 setting forth relevant attributes of the pharmacy 102 with respect to its participation in the system 100 as a buyer. The buyer subsystem 200 can also be used to define billing addresses and delivery addresses. The buyer subsystem 200 can allow the buyer to define rules 132 that pertain to the automated payments 134 using a variety of payment mechanisms 116 associated with the buyer.

In many embodiments of the buyer subsystem 200, the buyer can purchase a partial package size of a particular pharmaceutical product 106. In some embodiments, even a single capsule or tablet can be purchased. In some embodiments of the buyer subsystem 200, the buy subsystem 200 can include the functionality of a sticker that is printed by the buyer and placed on the package of the purchased pharmaceutical product(s) 106. The sticker or other form of identifier can be fastened to the purchased package identifying that package with the information on the system 100. For example, such a sticker could a written label identifying the source of the product 106, a numerical key identifying the specific transaction 128 through which the product 106 was obtained, a bar code that can be integrated with an inventory management tool 168, an RFID tag, or some other type of identification technique. In some embodiments, the label may include information about an FDA classification The buyer subsystem 200 can define price calculations 142 based on a time-based discount factor pertaining to the expiration date of a product 106. Automated notifications 130 pertaining to a particular transaction 128 or for all buying activities can be defined using the buyer subsystem 200. Historical attributes 136 pertaining the seller can be analyzed or prioritized with respect to the purchasing activities of the buyer. Different ways to calculate seller ratings can be configured by the buyer subsystem 200.

The buyer subsystem 200 can be used to monitor fulfillment activities and as well pending purchases while tabulating information from past transactions 128. The buyer subsystem 200 can configure applicable rules 130 that will trigger automated notifications 130, communications 120, payments 134, calculations 142, status changes 122, and other forms of automated system processing.

2. Seller Subsystem

A seller subsystem 202 can be used to conduct all of the interactions between a user 150 or pharmacy 102 acting as a seller with respect to the functionality of the system 100. In many ASP embodiments of the system 100, the ASP charges a pharmacy 102 as seller when a transaction 128 is consummated through use of the seller subsystem 202.

The seller subsystem 202 provides the mechanism by which products 106 and their attributes 108 become part of the available inventory 112 of the system 100. Acceptable payment mechanisms 116 can be defined in advance, and the financial accounts required for receiving such payments 134 can similarly be configured. Profiles 118 can be defined for the selling activities of the pharmacy 102 and its users 150. Communications 120, both automated and manual, can be sent and received during the search, negotiation, and fulfillment stages of a particular transaction 128. The impacts of status changes 122 with respect to the seller or the seller in a particular transaction can be configured using the seller subsystem 202. Transportation mechanisms 124 to be used in shipping products 106 can be defined and invoked using the seller subsystem 202. The fulfillment heuristics 138 invoked by the seller subsystem 202 can automatically identify relevant attributes of the shipped products 106, such as whether refrigerated packaging is required. The seller subsystem 202 can perform a wide variety of calculations pertaining to the pricing of product 106, including a variety of discounts that relate to the expiration date of product 106. In some embodiments of the seller subsystem 202, a time-based discount factor is used to increase the discount on a product 106 as the expiration date approaches.

The seller subsystem 202 can enable a seller to sell products 106 in less than a single package size/quantity of the product 106. Even a single table or capsule can be sold using the seller subsystem 202.

The seller subsystem 202 can provide for automatically performing a variety of fulfillment heuristics 138 that include the generating a shipment tracking ID, printing a packing checklist and a shipping label, adjusting inventory 112 after a product is shipped, generating notifications 130 at various stages in the transaction process, defining rules 132 that impact seller-related processing. The seller subsystem 202 can also be used to influenced how history-based processing is performed, including the rating of buyers. In many embodiments of the system 100, it is the seller subsystem 202 that is used by the ASP to charge its customers as only sellers are charged for use of the system 100, and they are only charged when a transaction 128 actually occurs.

3. Administrative Subsystem

An administrative subsystem 204 can be used by the system administrators to sustain the operation of the system 100. In many embodiments of the system 100, the administrative subsystem 204 provides for defining a wide range of potential rules 132 for configuring the functionality of the system 100 that can be selectively invoked and modified by buyers and sellers in variety of contexts.

B. Subsystem Configuration #2

Figure 4:
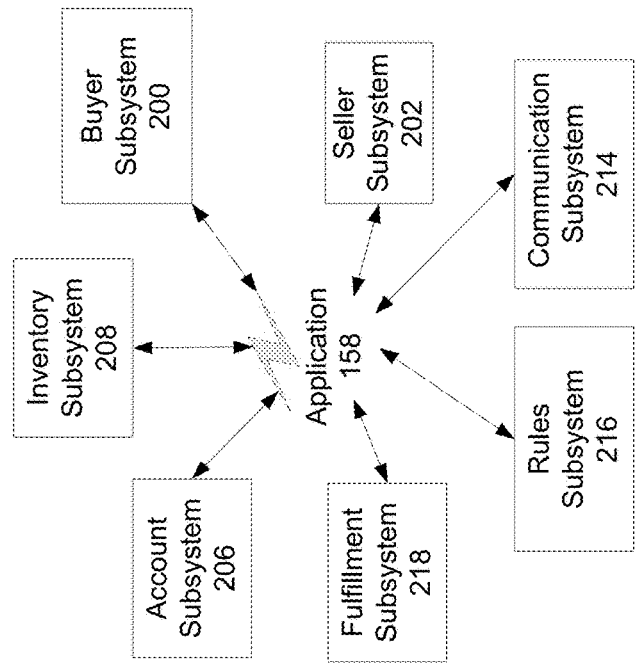
FIG. 4 is a block diagram illustrating an example of a subsystem-level view of the system.

FIG. 4 is a block diagram illustrating an example of a subsystem-level view of the system 100. In addition to the subsystems included in the illustration of FIG. 4, the configuration could also include the subsystems of FIG. 3 which are not illustrated in FIG. 4

1. Inventory Subsystem

The inventory subsystem 208 is used to add, update, and remove pharmaceutical products 106 from the inventory 112 of the system 100. In some embodiments of the inventory subsystem 208, certain products 106 added by certain sellers are only accessible to certain buyers in accordance with user-defined rules 132. In other embodiments, any potential buyer can view any and all products 106 added to the aggregate inventory 112 of the system 100. The inventory subsystem 208 can be used by sellers to provide pharmaceutical attributes 108 to the system 100 and potential buyers. In some embodiments of the inventory subsystem 208, historical attributes 136 pertaining to a particular product 106 or a particular user 150 or pharmacy 102 are saved within the inventory subsystem 208 because such attributes can impact the perceived desirability of a potential transaction 120 in the eyes of the buyer.

In some embodiments of the system 100, the inventory subsystem 208 can interface directly with the inventory management applications of buyers and sellers, allowing for the automated and near instantaneous updating of inventory 112 information.

2. Communication Subsystem

A communication subsystem 214 can be used to send and receive communications 120. Template communications 120 to be triggered automatically upon certain events or statuses 122 can also be created and maintained through the communication subsystem 214. For example, each stage of a transaction 120 can be associated with a template communication 120 that is populated with transaction-specific information before being sent to the other party. In many embodiments, the types of automated processing that can be performed by the communication subsystem 214 will depend on the types of rules 132 that can be configured using a rules subsystem 216.

5. Rules Subsystem

A rules subsystem 216 can be used to create, update, delete, view, and enforce the various rules 132 of the system 100. Some rules 132 are system-wide rules 132 defined by the administrator of the system 100 such as an ASP. Other types of rules 132 can be specific to a particular party, such as a user 150 or pharmacy 102, and still other rules can be specific to a particular party in a particular context, such as a rule 132 pertaining to a follow-up to a particular communication 120 or transaction 128.

6. Fulfillment Subsystem

A fulfillment subsystem 218 can be used to perform the necessary activities to consummate a transaction 128. Inventory 112 can be updated; payment mechanisms 116 invoked to pay the seller; transportation mechanisms 124 invoked to ship the purchased products 106; alerts 126 issued pertaining to the shipment of the products 106; history attributes 136 updated pertaining to the products 106, parties, and system 100 as a whole; checklists/package inserts printed; profiles 118 updated; statuses 122 updated; and the performance of other processes that can be useful to the fulfillment of consummated transactions 128.

7. Account Subsystem

The purchase and sale of pharmaceutical products 106 are regulated activities. An account subsystem 206 can be used to facilitate transactions by making the validation of legitimate buyers and sellers as quick, accurate, and efficient as possible. The account subsystem 206 can potentially interface directly with government databases containing licensing information. By validating a pharmacy 102 through the process of validating its account 110, the system 100 can avoid repeating from scratch a validation process each and every time a transaction 128 is initiated. The information used in the various validation heuristics 140 of the system 100 can be stored within the account subsystem 206 for subsequent reference by system 100 processing as desired. The account subsystem 206 is also the mechanism by which profiles 118 and users 150 are defined and authorized within the system 100.

V. Process-Flow Views

The system 100 can be implemented in such a manner as to support flexible interactions between buyers with sellers, sellers with buyers, and users 150 with the system 100. The system 100 need not pigeonhole users 150 into specific sequences of actions in order to achieve certain results. As stated above, the system 100 can be configured in a manner that promotes the ability of individual pharmacies 102 and users 150 to customize the system 100 to automate the system 100 in accordance with the preferences of the particular pharmacy 102 and/or user 150. In other words, the system 100 can be implemented in a manner that is very much user-driven.

A. Seller Process Flow

FIG. 5 is a flow chart diagram illustrating an example of a seller using the system 100 to sell a pharmaceutical product 106.

At 220, a pharmaceutical product 106 associated with a variety of pharmaceutical attributes 108 is added to the system 100 by the seller. In some embodiments of the system 100, this process interfaces with the inventory management software of the seller to automatically populate the system 100 with pharmaceutical attributes 108.

At 222, the seller can define required terms for a transaction 128 pertaining to one or more products 106. For example, the seller could require a particular payment mechanism 116, a particular shipment mechanism 124, attributes pertaining to a buyer such as history attributes 136 pertaining to the buyer's use of the system 100, and potentially any other data element that the system 100 can be cognizant of.

At 224, the seller exchanges one or more communications 120 with the buyer. Such communications 120 can be fully automated and rules-based in some embodiments of the system 100.

At 226, the transaction 128 is consummated. One or more fulfillment heuristics 138 can be invoked.

B. Buyer Process Flow

FIG. 6 is a flow chart diagram illustrating an example of a buyer using the system 100 to buy a pharmaceutical product 106.

At 230, a search of available inventory 230 is performed. In some embodiments of the system 100, ongoing and automated wishlists and watchlists can be scheduled using the system 100.

At 232, a buyer can submit an offer to a seller or otherwise communicate interest in a particular product 106 to the seller.

At 234, a buyer can exchange communications 130 with the seller or otherwise interact with the seller by interacting with the system 100.

At 236, the transaction 128 is consummated. One or more fulfillment heuristics 138 can be invoked.

C. Multi-Party Process Flow

FIG. 7 is a flow chart diagram illustrating an example of a pharmacy 102 registering and interacting with the system 100.

At 240, the pharmacy 102 registers with the system 100, obtaining a pharmacy account 110. This step can involve a variety of different validation heuristics 140 to confirm that the pharmacy 102 actually is a licensed pharmacy.

At 242, rules 132 can be customized for the pharmacy 102 and individual users 150 and profiles 118 defined with respect to the system 100.

At 244, the pharmacy 102 can upload their applicable inventory 112 to the database 160 of the system 100. In some embodiments, this process is done in a fully automated manner through an inventory management software application used by the pharmacy 102.

At 246, the pharmacy 102 can define automated notifications 130 with respect to its buying and/or selling activities.

At 248, the pharmacy 102 can initiate a communication 120 in response to a particular notification.

At 250, the pharmacy 102 can consummate a transaction 128 with another pharmacy 102 as a seller, buyer, or both.

At 252, the pharmacy 102 can initiate a fulfillment heuristic 138.

At 254, the pharmacy 102 can provide feedback information to be stored as history attributes 136 for future reference by the system 100 and other pharmacies 102 or users 150 of the system 100.

At 256, rules 130, profiles 118, statuses 122, and other data elements can be updated for future reference by the system 100.

D. Website Functionality Map

Figure 8:
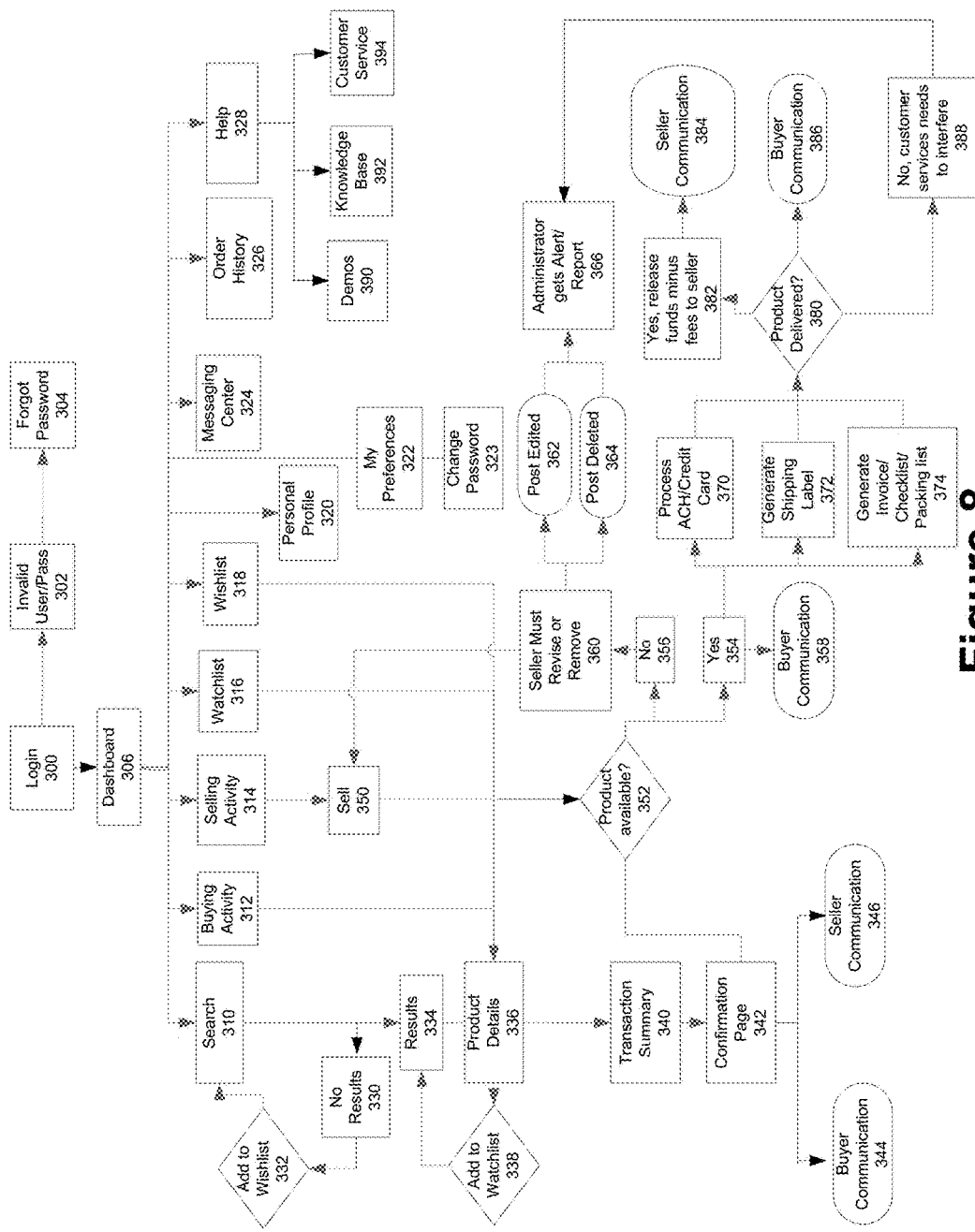
FIG. 8 is a process flow diagram illustrating an example of the system.

FIG. 8 is a multi-threaded process flow diagram illustrating an example of the functionality that can be performed through use of the system 100.

At 300, a user 150 can login to the system 100.

At 302, the system 100 can identify an invalid user ID or password.

At 304, a user 150 who has forgotten their password can initiate a process to authenticate the user 150 and provide the user 150 with access to the system.

At 306, the primary "dashboard" (see FIGS. 9a and 9b) of the system 100 can be accessed.

At 310, a search of the available inventory 112 of the system 100 can be performed.

At 312, a list of pending and/or past buying activity can be viewed, with the system 100 providing a user 150 with the ability to drill down to detailed information at 336.

At 314, a listing of pending and/or past selling activity can be viewed.

At 316, the "watchlist" of a pharmacy 102 can be viewed, updated, or added to.

At 318, the "wishlist" of a pharmacy 102 can be viewed, updated, or added to.

At 320, the personal profile 118 of the user 150 (in contrast to the pharmacy account 110 of the pharmacy 102) can be viewed, updated, added to, or deleted.

At 322, user preferences 322 can be created, updated, or deleted.

Passwords can be changed at 323.

At 324, the messaging center can be accessed in order to create new communications 120, view old communications 120, create template communications 120, and perform other communication-related functions.

At 326, order history and other history attributes 136 can be viewed.

At 328, the user 150 can access various "help" options including demos at 390, a knowledge base at 392, and a customer service screen at 394.

If the search at 310 fails to produce a result at 330, then the particular product 106 can be added to the wishlist at 332. Otherwise, the results of the search at 334 can be viewed in detail at 336 and added the watchlist at 338.

The product details at 336 can be accessed from either the buying activity screen at 312 or through the selling activity screen at 314. A transaction summary can be created at 340 which is followed up by a confirmation page at 342. A buyer communication can be sent at 344 and a seller communication can be sent at 346.

The availability of a particular product 106 is determined at 352, and it is not available at 356, the seller at 360 must remove the product from the available inventory 112 or otherwise revise the available inventory 112 before a selling transaction can be initiated at 350. A post can be edited at 362 or deleted at 364, which can trigger an alert 126 to an administrator at 366.

If a product 106 is available at 354, a buyer communication 358 can be triggered at 358, a payment 134 such as an ACH or credit card charge can be processed at 370, a shipping label generated at 372, and invoices, checklists, and packing lists created at 374.

The system 100 can track at 380 whether the product(s) 106 have been delivered yet. If delivery has occurred, funds (minus the fees to the administrator) can be released to the seller at 382 and a confirming notification 130 sent to the seller at 384. If the product(s) 106 at 380 have not yet been delivered, a buyer communication 130 can be triggered at 386 and in some cases, customer service on the part of the administrating entity invoked at 388.

The time period at which delivery confirmation is performed at what the resulting steps are can be defined as customized rules 132 by the individual users 150,

VI. Interface Views

The system 100 can incorporate a wide variety of different interfaces 154 that are accessed through a wide variety of different access devices 152. Interfaces 154 can be configured and customized in accordance to preferences defined in profiles 118 and pharmacy accounts 110 as well as the processing rules 132.

A. Dashboard View

Figure 9A:
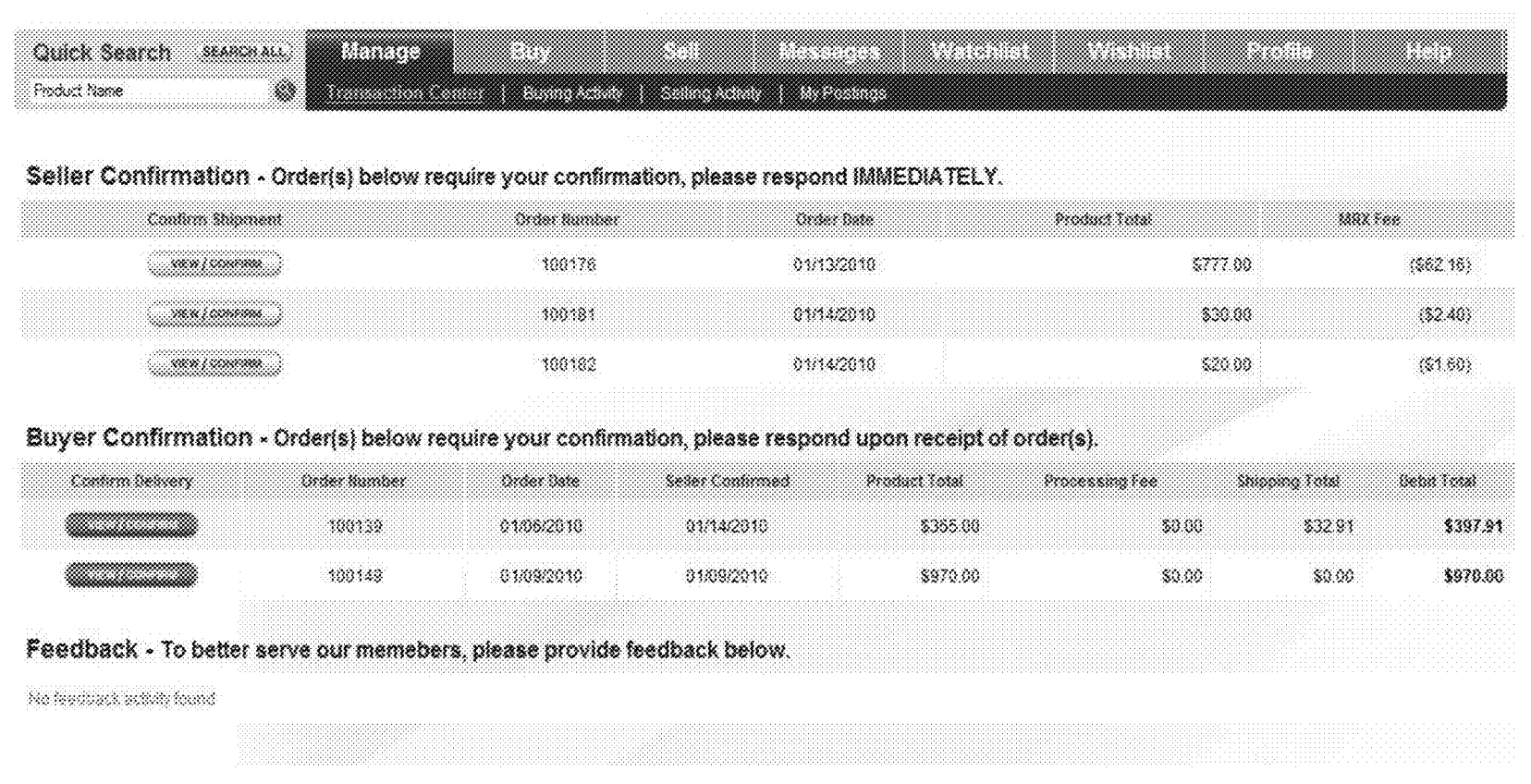

FIGS. 9a and 9b are in the aggregate, a screen print diagram illustrating an example of a "dashboard" that can be incorporated into the system 100. The dashboard view identifies pending orders from both a seller's perspective and a buyer's perspective. FIG. 9b represents portions of the dashboard adjacent to the right side of FIG. 9a. The dashboard screen can display a variety of different pharmaceutical attributes 108 and transaction attributes 128. Rules 132 can be defined to invoke automated processing that is triggered by a change in status 122 associated with one or more pending transactions 128 illustrated in the dashboard view.

B. Seller Confirmation

Figure 10A:
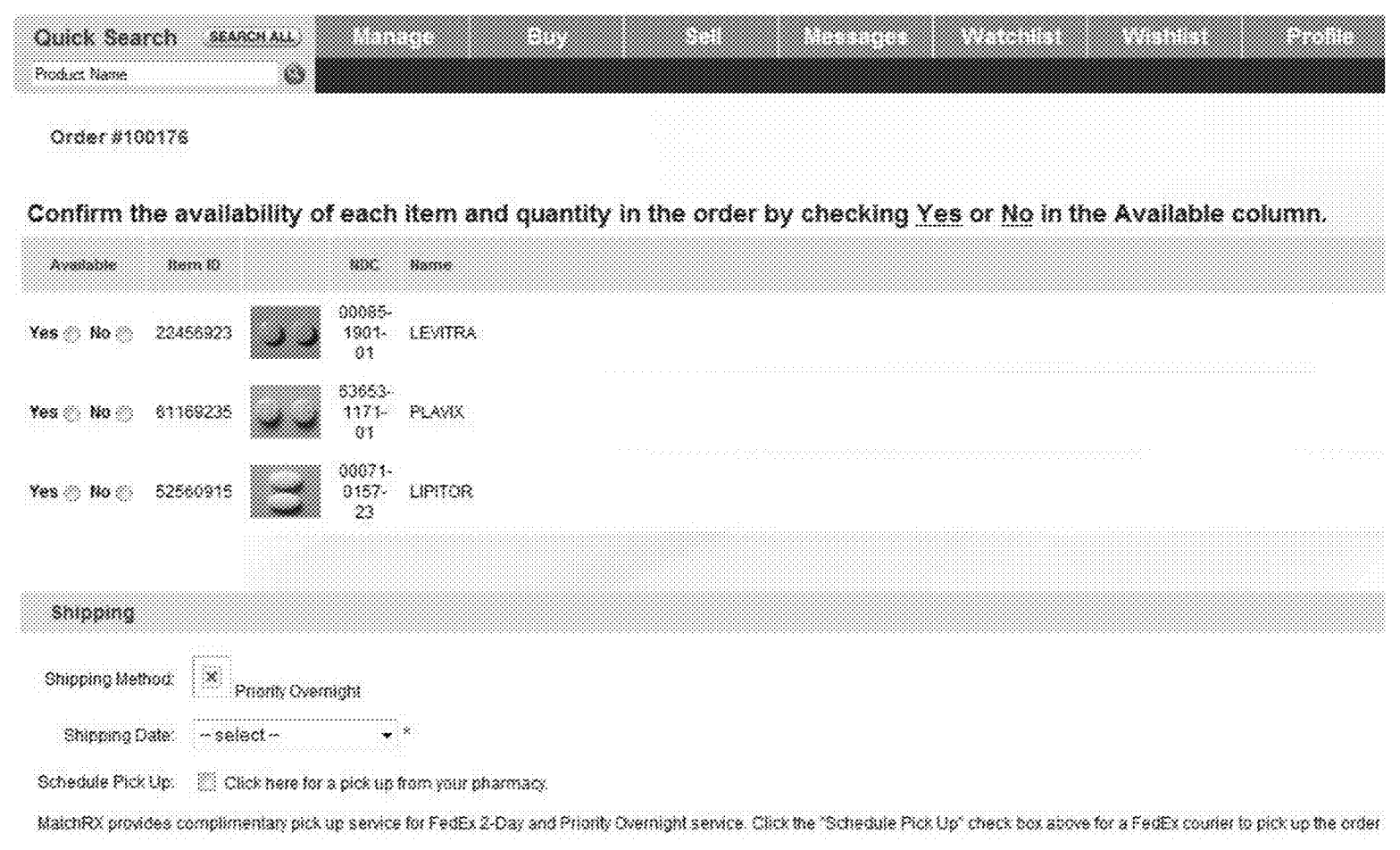
Figure 10B:
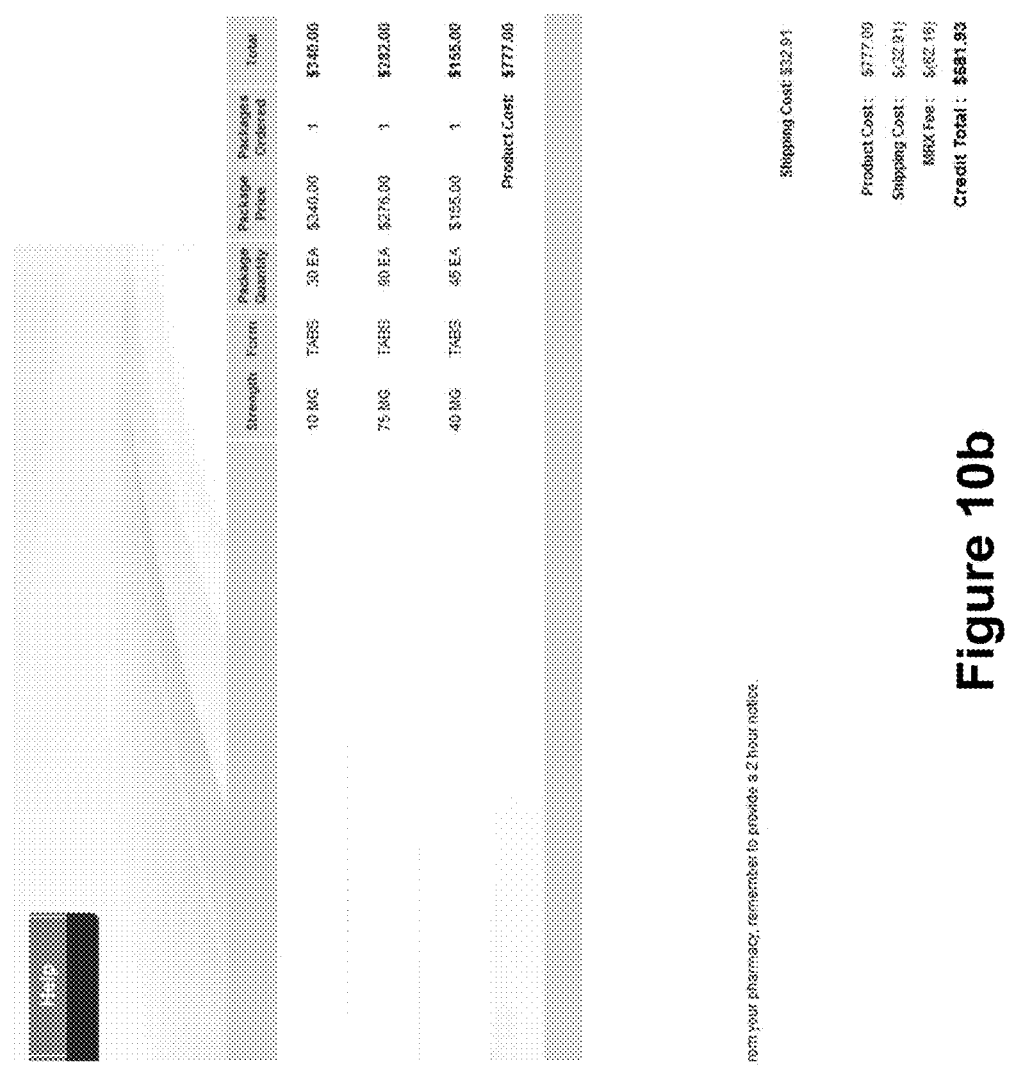

FIGS. 10a and 10b are in the aggregate, a screen print diagram illustrating an example of a screen that can be used to confirm the availability of a particular pharmaceutical product 106 in the inventory of the system 100 with respect to a particular proposed transaction 128 (i.e. order). FIG. 10a illustrates functionality for invoking transportation mechanisms 124. FIG. 10b illustrates data fields of the seller confirmation page that adjacent to the right side of FIG. 10a.

C. Buyer Search

Figure 11A:
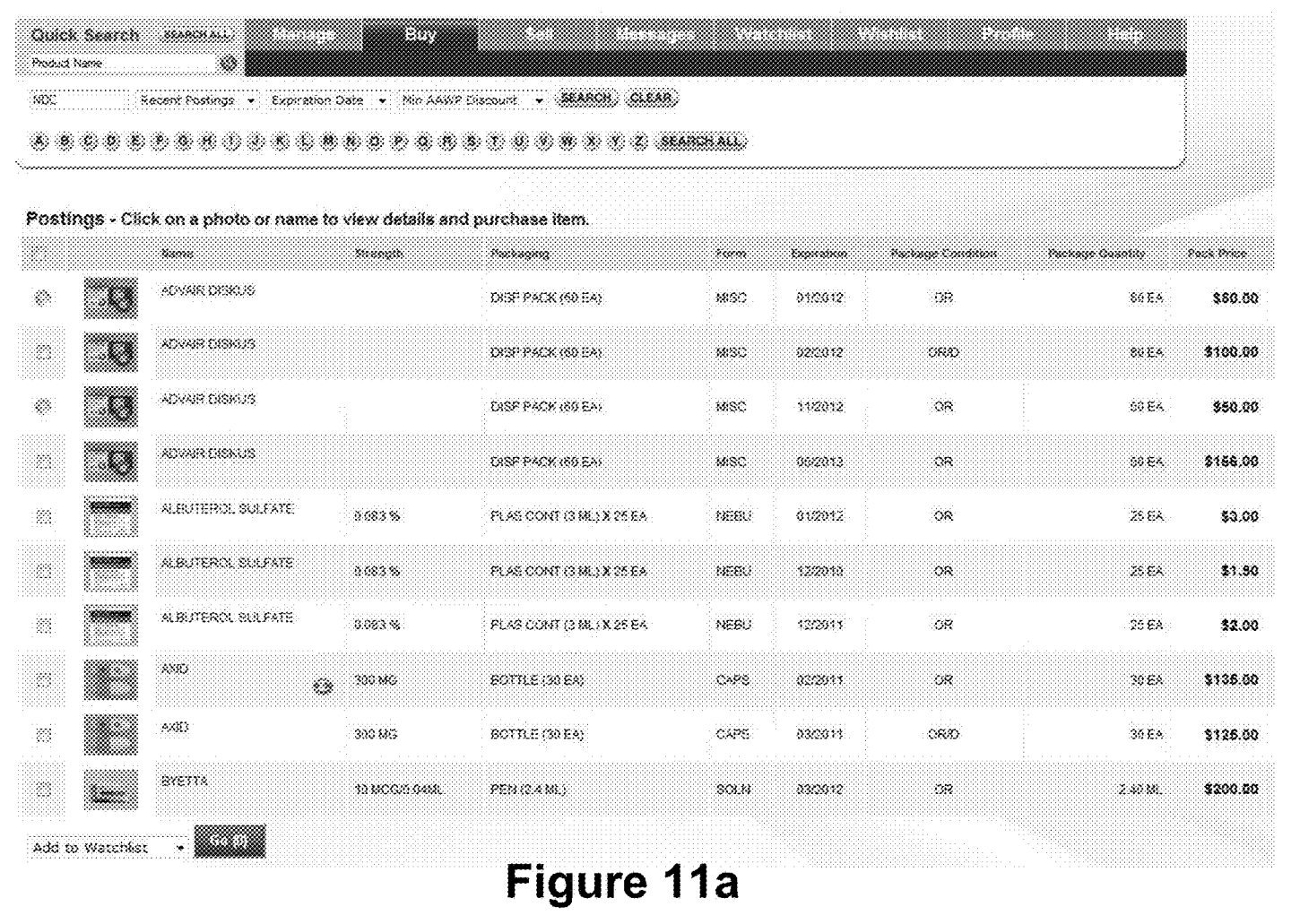
Figure 11B:
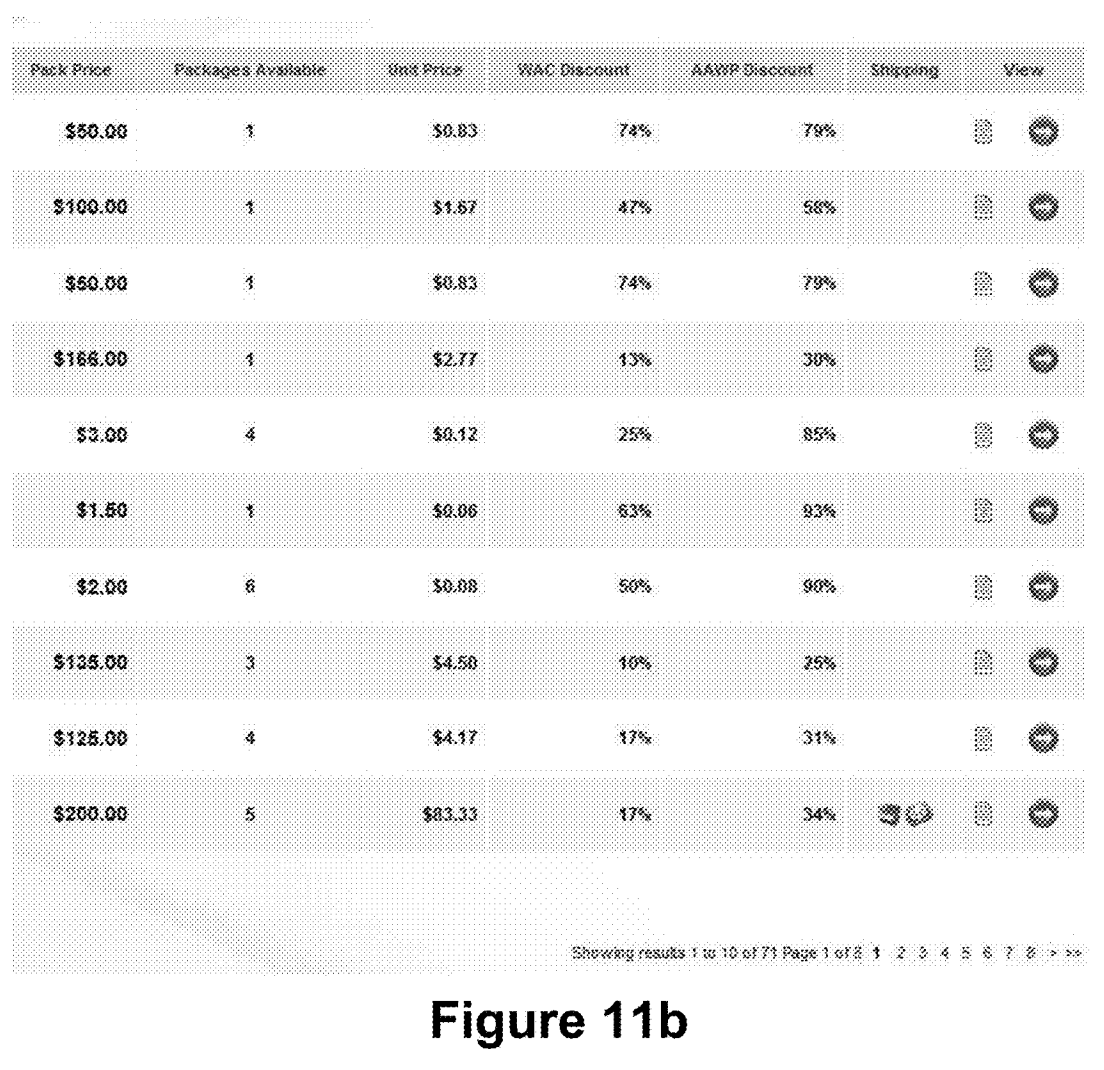

FIGS. 11a and 11b are in the aggregate, a screen print diagram illustrating an example of a screen that can be used by a buyer to search for desired pharmaceutical products 106. The ability of pharmaceutical products 106 to be searchable on this screen can in some embodiments of the system 100 be subject to rules 132 set by the seller adding those products 106 to the inventor of the system 100. FIG. 11b represents portions of the screen adjacent to the right side of FIG. 11a.

D. Seller Posting

Figure 12A:
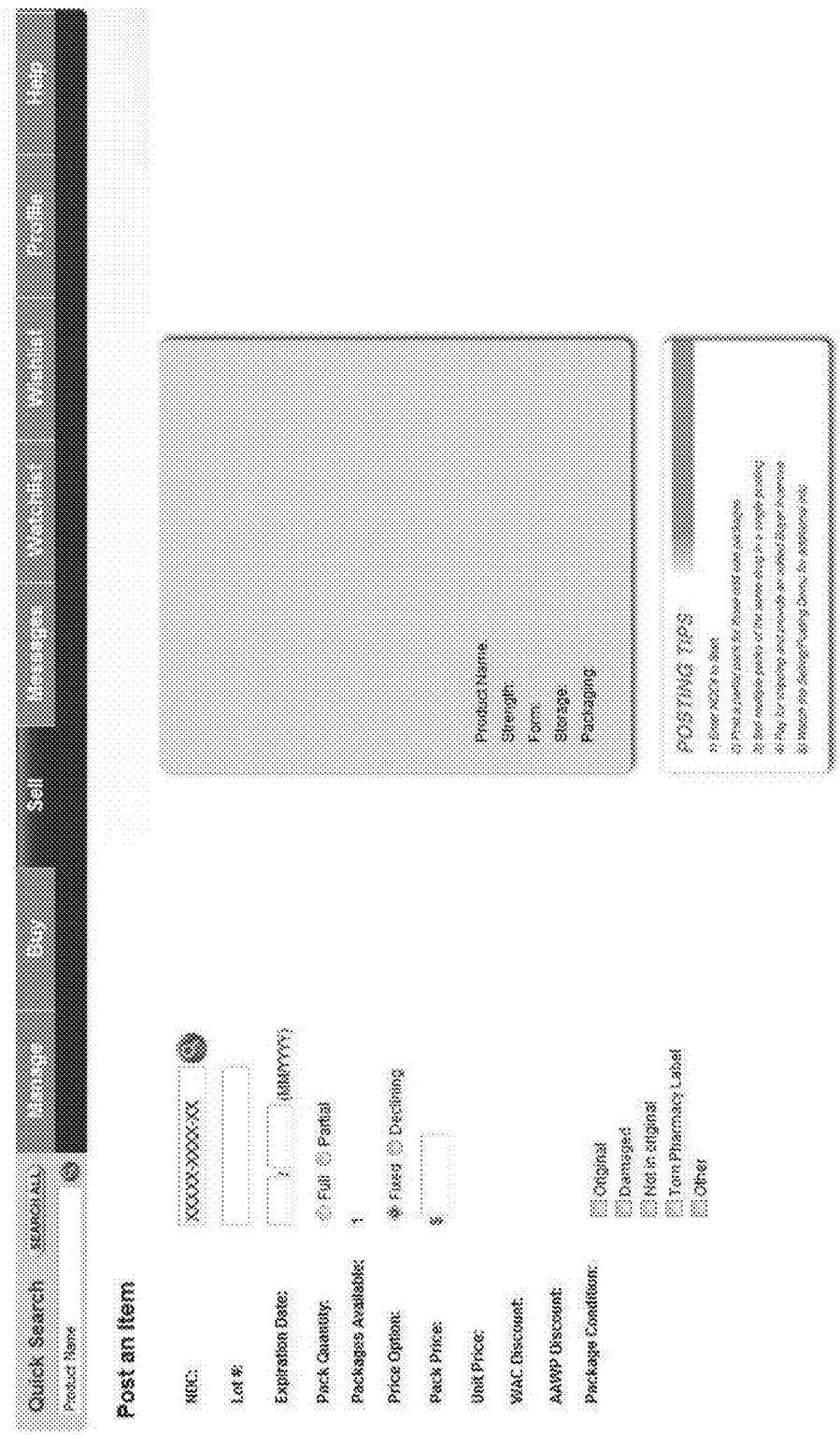
Figure 12B:
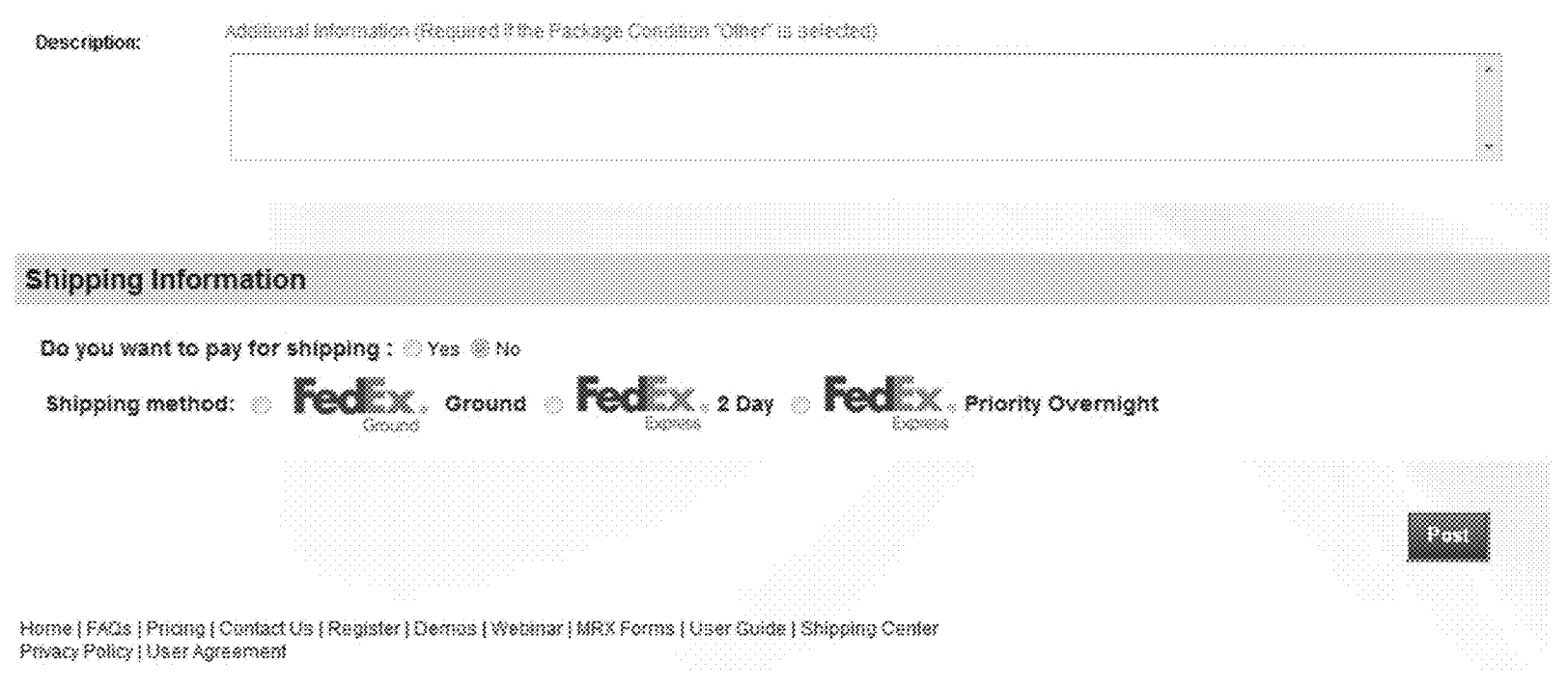
Figure 13A:
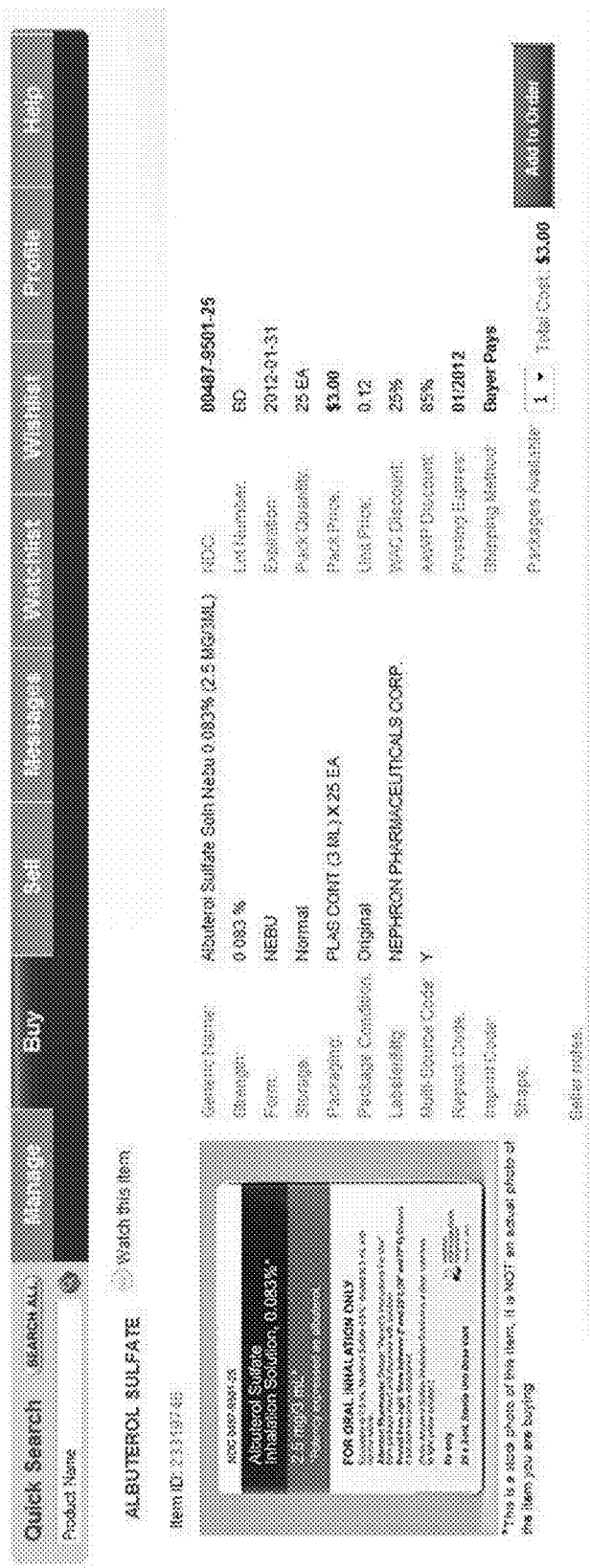
Figure 13D:
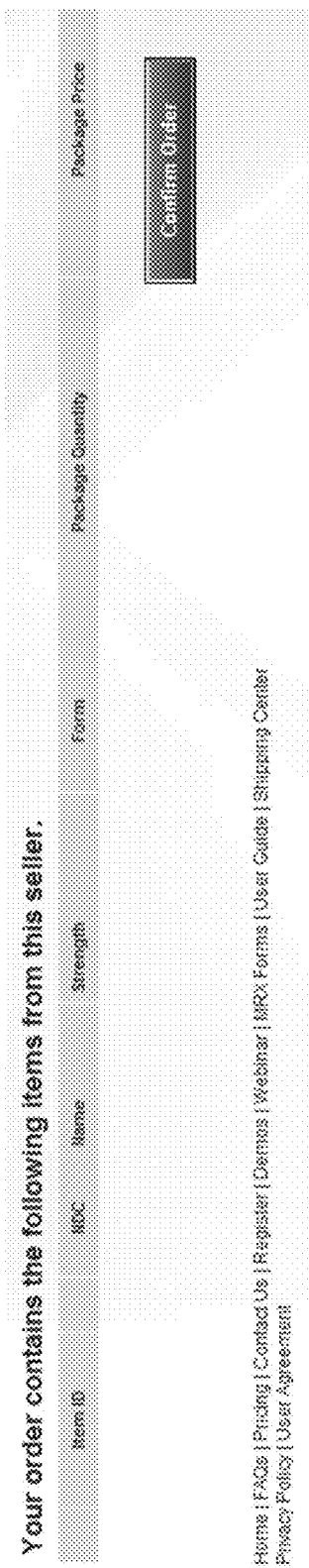
Figure 13E:
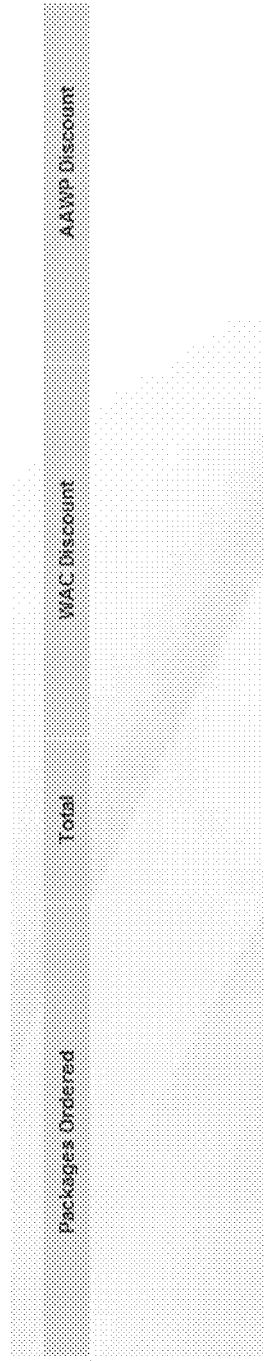

FIGS. 12a and 12b are in the aggregate, a screen print diagram illustrating an example of a screen that can be used by a seller to add to their inventory on the system 100. The screen can be used by sellers to define a variety of different pharmaceutical attributes 108 and transaction attributes. Among other data elements that can be set by this screen, a fixed or unfixed pricing option can be set. By selecting "declining", the price of a pharmaceutical product 106 can be automatically discounted in a predefined manner as the expiration date for that product 106 approaches. It is also noteworthy that partial package quantities of pharmaceutical products 106 can be entered onto the system 100. FIG. 12b is the portion of the screen adjacent to the bottom of the FIG. 12a illustration.

E. Buyer—Detail Product View

FIGS. 13a, 13b, 13c, 13d, and 13e are in the aggregate, a screen print diagram illustrating an example of screen that can be used by a buyer to display the details of a particular pharmaceutical product 106 (including product attributes 108 and transaction attributes) and additional items available from that same seller. FIGS. 13b, 13c, 13d, and 13e represent portions of the screen adjacent to the bottom of FIG. 13a, with FIGS. 13b, 13c, 13d, and 13e being positioned horizontally adjacent to each other from left to right.

Figure 14B:
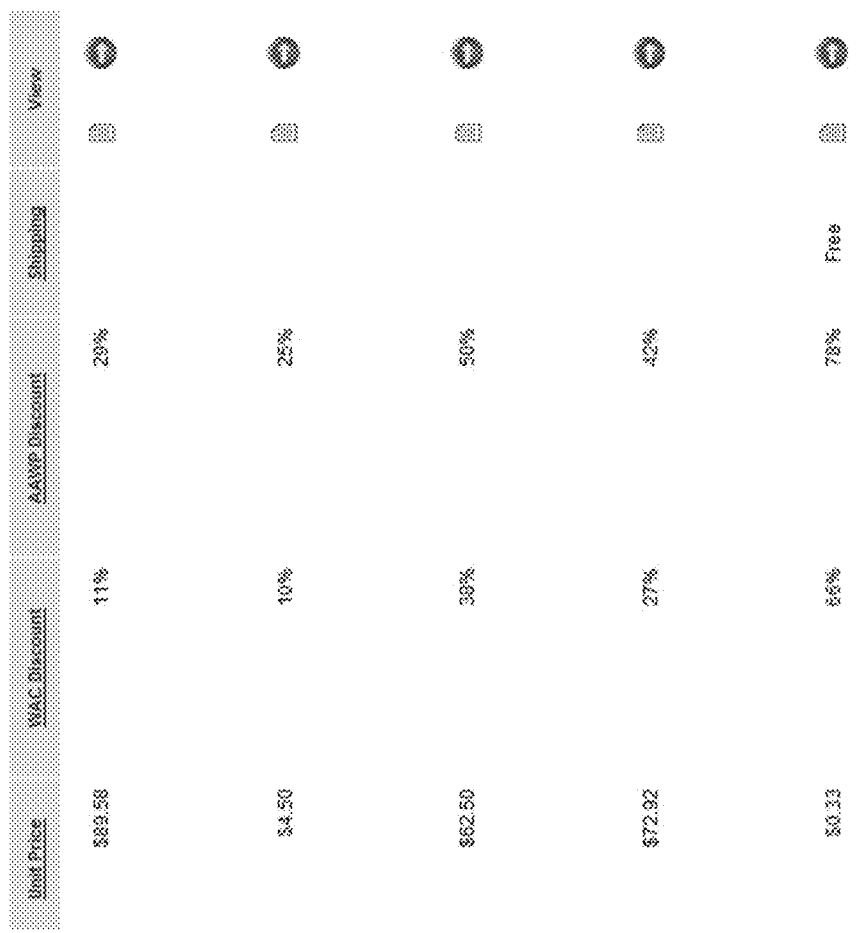

The screen illustrated in FIGS. 13a-13e allow a buyer to initiate the construction of an order or to add a product 106 to the watchlist illustrated in FIGS. 14a and 14b

F. Watchlist View

FIGS. 14a and 14b are in the aggregate, a screen print diagram illustrating an example of a "watchlist" screen. This screen can allow a buyer to monitor specific products 106 available in the virtual inventory 112 of the system 100. The ability of a particular product 106 to be viewable on the watchlist can be influenced by rules 132 defined by the holder/seller of the product 106. For example, a seller could automatically exclude the possibility of doing business with a particular buyer on the basis of past buyer behavior or other reasons. FIG. 14b represents the portion of the screen that is adjacent to the right side of FIG. 14a.

G. Wishlist View

Figure 15:
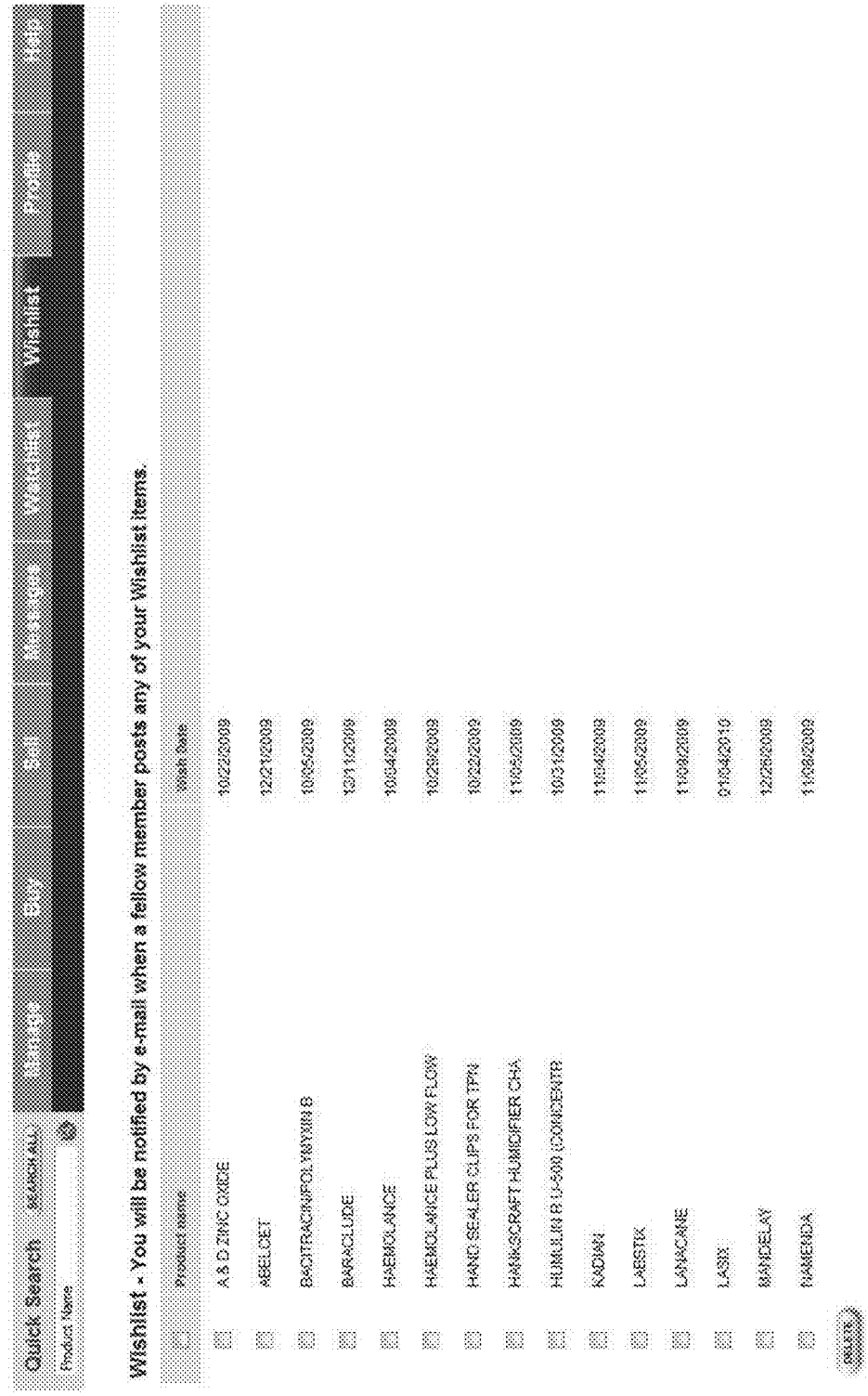
FIG. 15 is a screen print diagram illustrating an example of a "wishlist" screen.

FIG. 15 is a screen print diagram illustrating an example of a "wishlist" screen. The screen can be used to identify products 106 not available in any viewable inventory 112 that a buyer is potentially interested in obtaining. An automated notification 130 can be sent to the buyer when the desired product 106 is added to the system 100.

H. Package Checklist/Insert

Figure 16A:
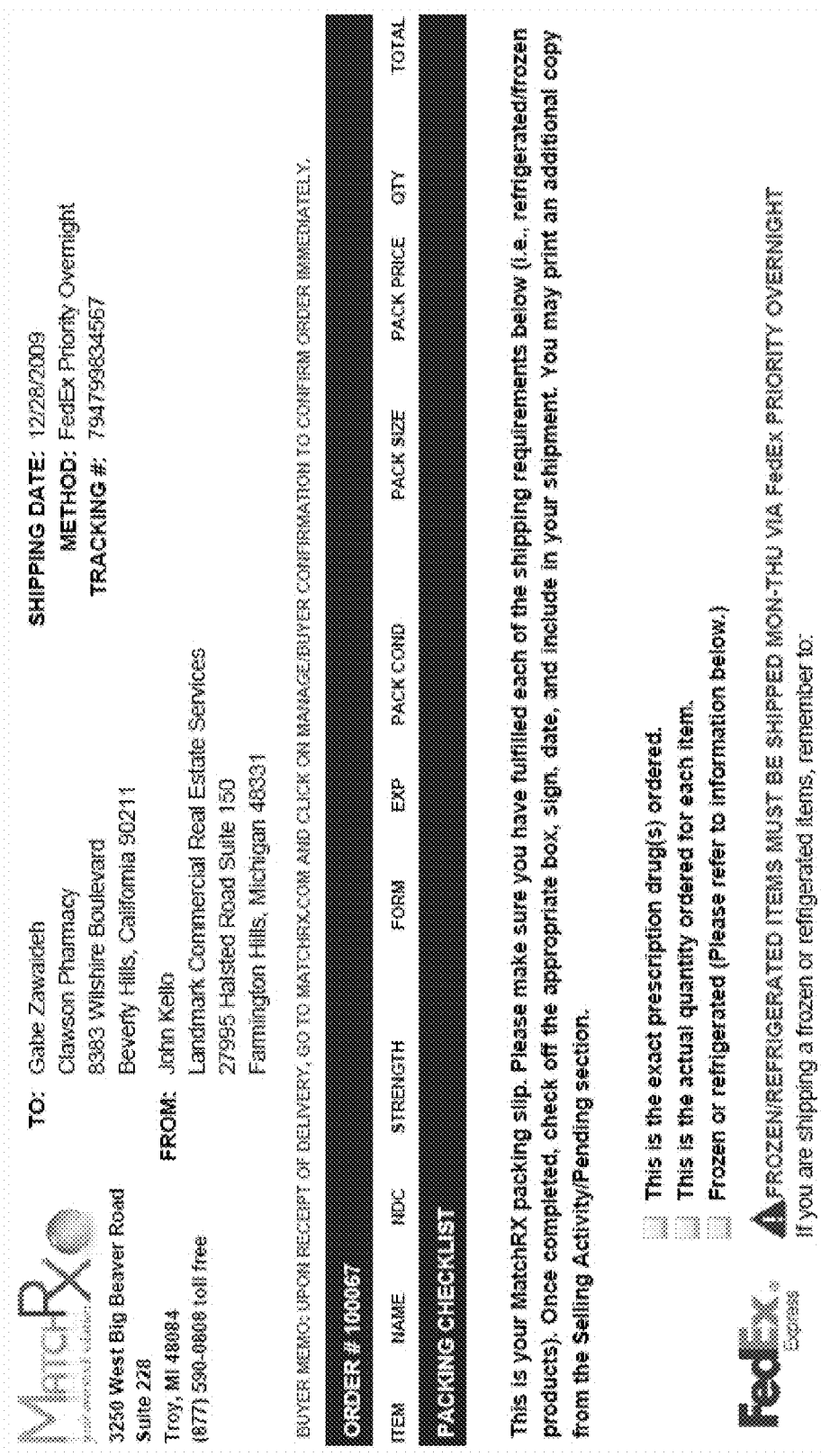
Figure 16C:
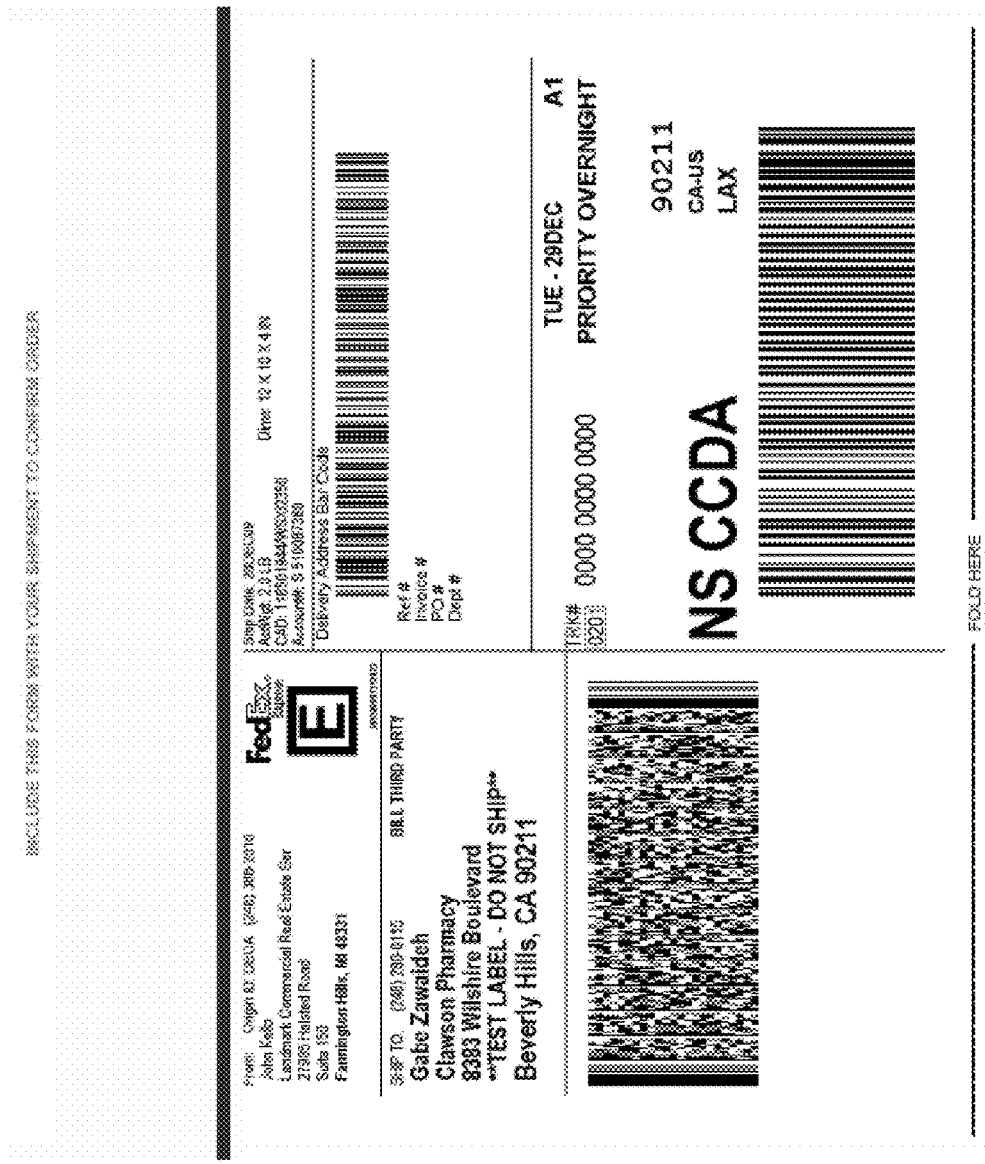

FIGS. 16a, 16b, and 16c are in the aggregate, an example of a packing checklist/insert that can be generated using the system 100. The checklist/insert can be generated automatically by the system 100 in accordance with the applicable rules 132 and preferences defined in the relevant profiles 118 and pharmacy accounts 110. The checklist/insert can be automatically configured to address particular attributes or combinations of attributes pertaining to the products 106, the transaction 128, or the contracting parties. FIG. 16b is adjacent to the bottom of FIG. 16a, and FIG. 16c is adjacent to the bottom of FIG. 16b. FIG. 16c is a printable shipment label that can be printed and fastened to the container containing the products 106 to the shipped.

I. Order Screen

Figure 17:
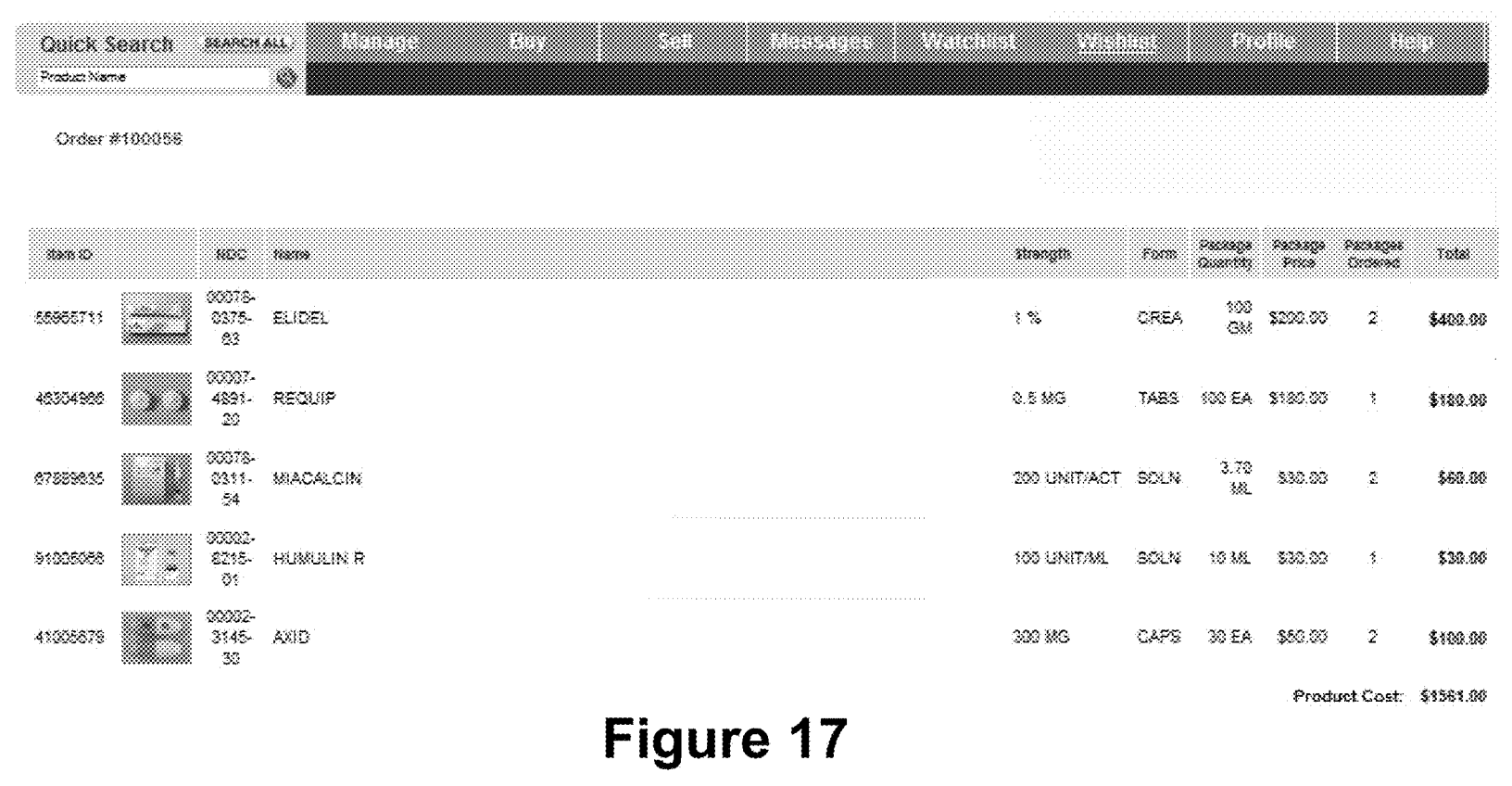

FIG. 17 is a screen print diagram illustrating an example of a multi-product 106 order being displayed using the system 100. Different embodiments of the system 100 can involve the display of different transaction attributes and different product attributes 108.

J. Invoice

FIG. 18 is a screen print diagram illustrating an example of an invoice that can be created using the system 100. The invoice can be sent automatically to the buyer in an electronic format. The sending of the invoice can be used to trigger a variety of automated processes by the system 100 and/or IT applications that integrate or interface with the system 100.

K. Communication Management

Figure 19A:
FIG. 19a is a screen print diagram illustrating an example of communications screen that can be incorporated into the system.

FIG. 19a is a screen print diagram illustrating an example of communications screen that can be incorporated into the system 100. As discussed above, the system 100 can be used to send and receive a wide variety of different communications 120 between users 150, as well as notifications 130 and alerts 126. The display of communications 120 on the screen can be influenced and configured through various processing rules 132, preferences expressed in one or more profiles 118, as well as preferences set at the pharmacy account 110 level. The system 100 can be configured to enable automated communications 120 generated on behalf of a user 150 or pharmacy 102 that are triggered by one or more statuses 122 that the system 100 is cognizant of.

Figure 19B:
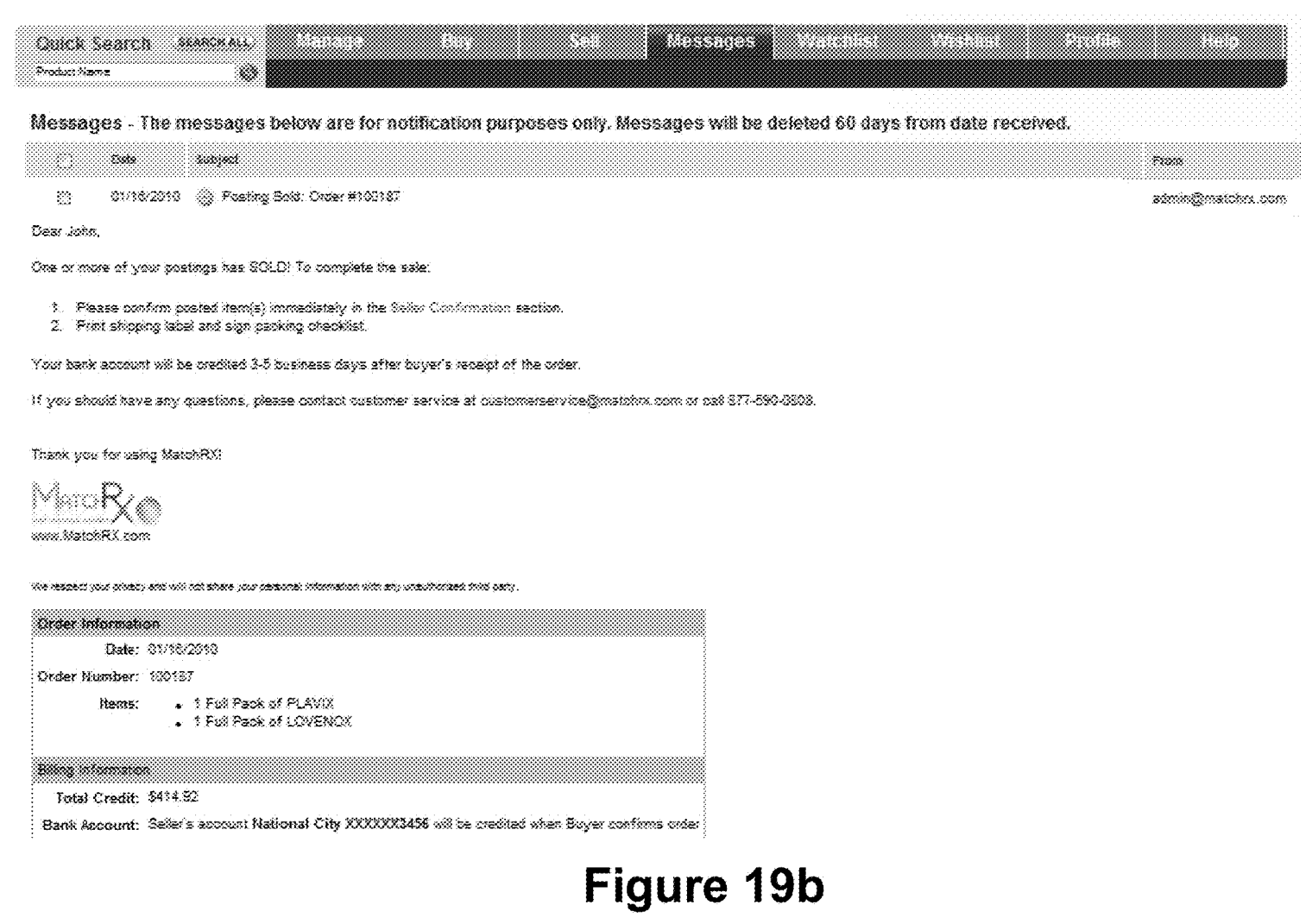

FIG. 19*b* is a screen print diagram illustrating an example of a communications screen with one of the communications being displayed in a detail view.

VII. Alternative Embodiments

The system can be implemented in a wide variety of different embodiments, configurations, and contexts. In accordance with the provisions of the patent statutes, the principles and modes of operation of this invention have been explained and illustrated in a variety of embodiments and configurations. However, it must be understood that this invention may be practiced otherwise than is specifically explained and illustrated without departing from its spirit or scope. The system can be implemented in a wide variety of different configuration using a wide variety of different information technology and other components in the processing of a wide variety of different elements and heuristics.

The invention claimed is:

1. A system comprising:
 (a) a server comprising a computer processor;
 (b) a computer program residing on the server, wherein the computer program provides for a sale of a pharmaceutical product from a first pharmacy account of a first pharmacy to a second pharmacy account of a second pharmacy, and wherein the computer program provides for a plurality of user interfaces including:
  i) a first user interface associated with the first pharmacy account at the first pharmacy; and
  ii) a second user interface associated with the second pharmacy account at the second pharmacy;
 (c) a database hosted by the server and accessible by the computer program via the server, wherein the database stores:
  i) a plurality of jurisdiction-based requirements pertaining to the sale and resale of a plurality of pharmaceutical products to and from a plurality of pharmacies in a plurality of jurisdictions, and wherein the plurality of jurisdictions includes a plurality of states, a first jurisdiction associated with the first pharmacy account and the first pharmacy, and a second jurisdiction associated with the second pharmacy account and the second pharmacy,
  ii) a validation heuristic which automatically confirms compliance of one or more of the plurality of jurisdiction-based requirements prior to the sale of the pharmaceutical product from the first pharmacy to the second pharmacy,
  iii) a plurality of configurable rules, wherein the sale of the pharmaceutical product is influenced by at least one of the plurality of configurable rules,
  iv) a plurality of pharmacy accounts which include the first pharmacy account and the second pharmacy account, and wherein the second pharmacy account is associated with a payment mechanism and a delivery address,
  v) the pharmaceutical product which is associated with the first pharmacy account, and
  vi) a fulfillment heuristic which provides for automatically printing a packing checklist at the first pharmacy associated with the first pharmacy account without human intervention;
 wherein the computer program automatically provides for paying the first pharmacy account through the payment mechanism without any human intervention; and
 wherein the computer program automatically provides for identifying a shipping method and generating a shipment tracking number and a shipping label without any human intervention, wherein a cost of shipping is automatically added to a price before the sale of the pharmaceutical product is consummated, and wherein the first user interface provides for printing the shipping label at the first pharmacy associated with the first pharmacy account.

2. The system of claim 1, wherein the computer processor:
 adds the pharmaceutical product to an inventory stored on the database of a plurality of available pharmaceutical products, wherein at least one of the available pharmaceutical products is associated with a refrigeration requirement, and wherein at least one of the available pharmaceutical products is associated with a partial package quantity;
 searches the database for a desired pharmaceutical product using a plurality of search criteria submitted through a search tool;
 stores a plurality of template communications and a plurality of profiles on the database;
 notifies a buyer of the desired pharmaceutical product;
 notifies a seller of a proposed transaction that includes the desired pharmaceutical product;
 identifies the payment mechanism and the shipping method for the proposed transaction, wherein the shipping method is a private carrier with a website configured to provide automated tracking information;
 calculates a discount pertaining to a wholesale acquisition (WAC) price or an average of an average wholesale price (AAWP) price; and
 automatically invokes the fulfillment heuristic that is selectively influenced by at least one of the configurable rules.

3. The system of claim 1, further comprising a plurality of remote access devices accessing the server through a World Wide Web and a printer remote from the server that is accessible from at least one of the remote access devices;
 wherein the plurality of remote access devices provide for initiating a registration heuristic;
 wherein the computer program provides for performing the validation heuristic prior to a creation of the plurality of pharmacy accounts;
 wherein the database provides for storing a plurality of pharmacy license attributes for each of the plurality of pharmacy account;
 wherein the database provides for storing a copy of a pharmacy license associated with at least one the pharmacy accounts;
 wherein at least one of the plurality of pharmaceutical products is a prescription medication regulated by the food and drug administration (FDA);
 wherein the database provides for storing a quantity metric of the pharmaceutical product which includes a quantity which is less than a full package size of at least one of the plurality of pharmaceutical products;
 wherein the computer program provides for automatically invoking the fulfillment heuristic that is selectively influenced by a user-defined rule;

wherein the server is operated by an application service provider (ASP) who is not a pharmacy;

wherein the printer provides for printing a sticker adapted to be attached to a container for at least one of the plurality of pharmaceutical products; and wherein the registration heuristic provides for an automated validation of a pharmacy attribute by communicating with a government database outside the system.

4. The system of claim 1, wherein the database provides for storing a plurality of transaction attributes from the first user interface; and wherein the plurality of transaction attributes includes the price for the pharmaceutical product, an expiration date associated with the pharmaceutical product, an available quantity associated with the pharmaceutical product, and a time-based discount factor associated with the pharmaceutical product that is defined by at least one of said the plurality of configurable rules defined by the first pharmacy account.

5. The system of claim 1, wherein the first user interface provides for viewing a plurality of history attributes associated with the second pharmacy account; and wherein the second user interface provides for viewing a plurality of history attributes associated with the first pharmacy account.

6. The system of claim 5, wherein at least one of the plurality of pharmacy accounts is associated with a rating that is viewable from at least one of the plurality of user interfaces; and wherein the rating is influenced by the plurality of history attributes relating to the pharmacy account associated with the rating.

7. The system of claim 1, wherein the computer program provides for receiving a plurality of search attributes from the second user interface; and wherein the plurality of search attributes includes a minimum discount percentage and a national drug code (NDC).

8. The system of claim 1, wherein the database provides for storing the plurality of pharmaceutical products;

wherein at least one of the plurality of pharmaceutical products is associated with a refrigeration flag;

wherein at least one of the pharmaceutical products is associated with a fixed price;

wherein at least one of the pharmaceutical products is associated with a declining price;

wherein at least one of the pharmaceutical products is associated with a minimum discount percentage;

wherein at least one of the pharmaceutical products is associated with a national drug code (NDC); and wherein the computer processor invokes a minimum discount validation heuristic.

9. The system of claim 1, wherein the plurality of pharmacy accounts are not charged a subscription fee by an application service provider (ASP);

wherein the first pharmacy account is not charged for selling the pharmaceutical product;

wherein the first pharmacy account is not charged for storing the pharmaceutical product on the database; and wherein the second pharmacy account is not charged for viewing the pharmaceutical product on the second user interface.

10. The system of claim 1, wherein a desired pharmaceutical product is received through the second user interface and stored on the database;

wherein the computer program automatically sends an availability notification to the second pharmacy account when the desired pharmaceutical product becomes available on the database;

wherein the first pharmacy account is in the first jurisdiction subject to a first jurisdictional rule; and wherein the second pharmacy account is in the second jurisdiction subject to a second jurisdictional rule.

11. The system of claim 1, wherein the database includes a plurality of user profiles associated with the first pharmacy account and the second pharmacy account, and a plurality of history attributes relating to at least one of the plurality of user profiles; and wherein the plurality of configurable rules include at least one user-level rule and at least one pharmacy-level rule.

12. The system of claim 1, wherein the first user interface and the second user interface provide for viewing a plurality of pending sales, a plurality of pending purchases, a seller rating, a plurality of past sales, and a plurality of past purchases.

13. The system of claim 12, wherein the database further provides for storing a plurality of user profiles;

wherein the first pharmacy account and the second pharmacy account are each associated with at least one of said the plurality of user profiles;

wherein a plurality of notification rules are selectively influenced by the plurality of user profiles;

wherein at least one of the plurality of user profiles is associated with at least one of the configurable rules; and wherein the first pharmacy account and the second pharmacy account each include a default payment mechanism and a default shipment mechanism.

14. The system of claim 1, wherein the database provides for storing a plurality of template communications, a plurality of configurable notification rules, and a plurality of configurable template notifications;

wherein at least one of the plurality of configurable notification rules is triggered by a seller action;

wherein at least one of the plurality of configurable notification rules is triggered by a seller omission;

wherein at least one of the plurality of configurable notification rules is triggered by a buyer action;

wherein at least one of said the plurality of configurable notification rules is triggered by a buyer omission;

wherein at least one of the configurable notification rules is triggered by a future expiration of the pharmaceutical product;

wherein at least one of the configurable notification rules is triggered by a shipment status; and wherein at least one of the configurable notification rules is triggered by a payment.

15. An information technology system for facilitating a resale of a plurality of available pharmaceutical products among a plurality of pharmacies, comprising:

(a) a server comprising a computer processor;

(b) a computer program residing on the server, wherein the computer program provides for the resale of a pharmaceutical product from a first pharmacy account of a first pharmacy to a second pharmacy account of a second pharmacy;

(c) a database hosted by the server and accessible by the computer program via the server, wherein the database stores:

(i) an account subsystem, wherein the account subsystem provides for a plurality of pharmacy accounts associated with the plurality of pharmacies, wherein the plurality of pharmacy accounts includes the first pharmacy account and the second pharmacy account, the plurality of pharmacies includes the first pharmacy and the second pharmacy, and the first pharmacy account is associated with the first pharmacy and the second pharmacy account is associated with the second pharmacy;

(ii) an inventory subsystem, wherein the inventory subsystem provides for identifying a plurality of pharmaceutical products as the plurality of available pharmaceutical products, wherein the plurality of available pharmaceutical products include a plurality of product attributes, and wherein the plurality of product attributes include an expiration date, a refrigeration requirement, a national drug code (NDC), a price, a price type, a package size, a discount percentage, and an owner;

(iii) a seller subsystem, wherein the seller subsystem provides for adding, updating, and removing the plurality of available pharmaceutical products from the inventory subsystem by a seller at the first pharmacy, wherein the seller is the owner;

(iv) a buyer subsystem, wherein the buyer subsystem provides for searching the inventory subsystem using a plurality of search attributes and initiating a transaction for a purchase of one or more the plurality of available pharmaceutical products by a buyer at the second pharmacy; and (v) a fulfillment subsystem, wherein the fulfillment subsystem provides for automatically identifying a shipping method and generating a shipment tracking number and a shipping label without any human intervention, printing the shipping label at the first pharmacy associated with the seller and first pharmacy account, automatically printing a packing checklist at the first pharmacy associated with the seller and without any human intervention,, wherein the fulfillment subsystem provides for automatically processing a payment to the seller without any human intervention, and wherein the fulfillment subsystem provides for automatically transmitting a portion of the payment to an operator of the system without any human intervention.

16. The information technology system of claim 15, wherein the account subsystem provides for an automated registration validation heuristic, wherein the fulfillment subsystem provides for generating a plurality of automated notifications, and wherein the plurality of pharmaceutical products are prescription medications.

17. The information technology system of claim 15, wherein the account subsystem provides for automatically identifying a legal requirement necessitating the use of at least one of: (a) a licensed wholesaler; and (b) a reverse distributor; and
wherein the fulfillment subsystem uses at least one of: (a) a wholesaler account; and (b) a reverse distributor account, to facilitate consummation of the transaction.

18. A method for selling a pharmaceutical product from a first pharmacy to a second pharmacy, wherein the method comprises:

a) logging into a system by a user of the second pharmacy, the system having:
(i) a server comprising a computer processor;
(ii) a computer program residing on the server and having a plurality of user interfaces, including a first user interface associated with a first pharmacy account at a fist pharmacy and a second user interface associated with a second pharmacy account at a second pharmacy; and
(iii) a database hosted by the server and accessible by the computer program via the server, the database storing:
a plurality of jurisdiction-based requirements pertaining to a sale and resale of a plurality of pharmaceutical products to and from a plurality of pharmacies in a plurality of jurisdictions, and wherein the plurality of jurisdictions includes a plurality of states, a first jurisdiction associated with the first pharmacy account and the first pharmacy, and a second jurisdiction associated with the second pharmacy account and the second pharmacy,
available inventory which includes the pharmaceutical product;
a validation heuristic,
a plurality of configurable rules;
a plurality of pharmacy accounts which include the first pharmacy account and the second pharmacy account, and
a fulfillment heuristic;

b) submitting search criteria for the pharmaceutical product in a search tool by the user via a second user interface;

c) automatically searching the available inventory stored in the database for the search criteria using the computer processor;

d) automatically notifying the user of availability of the pharmaceutical product via the second interface;

e) automatically notifying the first pharmacy via the first interface of an offer from the second pharmacy to purchase the pharmaceutical product;

f) automatically confirming compliance of one or more of the plurality of jurisdiction-based requirements by the first pharmacy and the second pharmacy prior to the sale of the pharmaceutical product from the first pharmacy to the second pharmacy through the validation heuristic;

g) automatically identifying a shipping method, generating a printed packaging checklist at the first pharmacy, generating a shipment tracking number, and generating a shipping label without any human intervention through the fulfillment heuristic; wherein the first user interface provides for printing the shipping label at the first pharmacy associated with the first pharmacy account;

h) automatically adding a cost of shipping to a price of the pharmaceutical product before the sale is consummated; and i) automatically paying the first pharmacy account with a payment mechanism associated with a second pharmacy account through the fulfillment heuristic and without any human intervention.

19. The method of claim 17, wherein the first pharmacy uploads their applicable inventory, including the pharmaceutical product, into the available inventory in the database.

* * * * *